(12) United States Patent
Durst et al.

(10) Patent No.: US 7,488,722 B2
(45) Date of Patent: Feb. 10, 2009

(54) ANXIOLYTIC MARCGRAVIACEAE COMPOSITIONS CONTAINING BETULINIC ACID, BETULINIC ACID DERIVATIVES, AND METHODS

(75) Inventors: Tony Durst, Ottawa (CA); Zulfiquar Merali, Ottawa (CA); John T. Arnason, Ottawa (CA); E. Pablo Sanchez-Vindas, Heredia (CR); Luis J. Poveda Alvarez, Alajuela (CR)

(73) Assignee: University of Ottawa, Ottawa, Ontario (CA)

( * ) Notice: Subject to any disclaimer, the term of this patent is extended or adjusted under 35 U.S.C. 154(b) by 659 days.

(21) Appl. No.: 10/476,716

(22) PCT Filed: May 10, 2002

(86) PCT No.: PCT/CA02/00695

§ 371 (c)(1),
(2), (4) Date: May 17, 2004

(87) PCT Pub. No.: WO02/091858

PCT Pub. Date: Nov. 21, 2002

(65) Prior Publication Data

US 2004/0235805 A1    Nov. 25, 2004

(51) Int. Cl.
*A61K 36/00* (2006.01)
*A61P 25/22* (2006.01)
(52) U.S. Cl. .................. 514/169; 514/172; 424/725
(58) Field of Classification Search ............... 514/169, 514/172
See application file for complete search history.

(56) References Cited

U.S. PATENT DOCUMENTS

| | | | |
|---|---|---|---|
| 5,468,888 A | 11/1995 | Bouboutou et al. | 554/58 |
| 5,529,769 A | 6/1996 | Cho et al. | 424/74 |
| 5,589,182 A | 12/1996 | Tashiro et al. | 424/423 |
| 5,658,947 A | 8/1997 | DasGupta et al. | 514/510 |
| 5,679,828 A | 10/1997 | Lee et al. | 560/116 |
| 5,869,535 A | 2/1999 | Pezzuto et al. | 514/640 |
| 6,046,231 A | 4/2000 | Kosmeder, II et al. | 514/456 |
| 6,048,847 A | 4/2000 | Ramadoss et al. | 514/169 |
| 6,124,362 A | 9/2000 | Bradbury et al. | 514/569 |
| 6,369,109 B1 | 4/2002 | Debatin et al. | 514/569 |

FOREIGN PATENT DOCUMENTS

| | | |
|---|---|---|
| DE | 19713768.7 | 10/1998 |
| EP | 0943620 | 9/1999 |
| JP | 44031593 | 9/1967 |
| JP | 57031620 | 2/1982 |
| JP | 6-31593 | 2/1994 |
| JP | 2000-247993 | * 9/2000 |
| WO | WO 96/39033 | * 12/1996 |

OTHER PUBLICATIONS

Schultes R. E., "De Plantis Toxicariis E Munco Novo Tropicale Commentationes XXVI. Ethnopharmacological Notes on the Flora of Northwestern South America" Bot. Mus. Leafl. Harv. Univ. (1980) vol. 28, No. 1, p. 1-45.
Chaudhuri, P.K., "Constituents of the Flowers of *Echinops Echinatus*" Fitoterapia, (1988), vol. 59, No. 2, p. 150-151, 5 REF. ISSN: 0367-326X, XP001096391, Cent. Inst. Medical & Aromatic Plants, Lucknow 226 016, India. abstract.
American Psychiatric Association, (1994), "Diagnostic and statistical manual of mental disorders, 4th Ed. (DMS-IV)", Washington, D.C., p. 393-445.
Siddiqui, S., et al., "Oleanderol, A New Pentacyclic Triterpene from the Leaves of Nerium Oleander", J. Nat. Prod. (1988) vol. 51, No. 2, p. 229-233.
File, S. E., "The use of social interaction as a method for detecting anxiolytic activity of chlor-diazepoxide-like drugs", In Current Protocols in Neuroscience, p. 8.3.3-8.3.4, John-Wiley & Sons.
Pellow, S., et al., "Validation of open:closed arm entries in an elevated plus-maze as a measure of anxiety of the rat", (1985), In Current Protocols in Neuroscience, p. 8.3.6-8.3.8, John-Wiley & Sons.
Vogel, J. R., et al., A simple and reliable conflict procedure for testing anti-anxiety agents, (1971), In Current Protocols in Neuroscience, p. 8.3.10-8.3.20, John-Wiley & Sons.
Weiss, S. R. B., et al., "Animal Models of Anxiety" (1990), In Neurobiology of Panic Disorder, p. 3-27, Maryland: Alan R. Liss, Inc.
Fujioka, T., et al., "anti-AIDS Agents, 11.[1] Betulinic Acid and Platanic Acid as Anti-HIV Principles from Syzigium Claviflorum, and the Anti-HIV Activity of Structurally Related Triterpenoids", J. Nat. Prod. (1994), vol. 57, No. 2, p. 243-247.
Aplin, R. T., et al., "The Chemistry of Triterpenes and Related Compounds. Part XLIII.* The Constituents of the Bark of Platanus × hybrida Brot. and the Structure of Platanic Acid", J. Chem. Soc. (1963) p. 3269-3273.
Vystrčil, et al., "Triterpenes. XVI.* . . . ", Coll. Czech. Chem. Comm. (1970) vol. 35, p. 295-311.
Kessler, R. C., et al. (1994) "Lifetime and 12-Month Prevalence of DSM-III-R Psychiatric Disorders in the United States: Results from the National Comorbidity Survey", Archives of General Psychiatry, vol. 51, p. 8-19.
Alloy, L. B., et al. (1999) Abnormal Psychology: Current Perspectives, p. 150-175, McGraw-Hill, Boston, MA.

(Continued)

*Primary Examiner*—Sreeni Padmanabhan
*Assistant Examiner*—Sahar Javanmard
(74) *Attorney, Agent, or Firm*—DLA Piper LLP (US)

(57) ABSTRACT

Pharmaceutical compositions for preventing or treating anxiety, comprising betulinic acid or derivatives thereof are provided. Methods for preventing or treating anxiety with betulinic acid or derivatives thereof are also provided. The invention further provides betulinic-acid containing preparations of plants of the family Marcgraviaceae having anxiolytic activity and methods for making such extracts and using them to prevent or treat anxiety in a subject.

13 Claims, 8 Drawing Sheets

OTHER PUBLICATIONS

Evers, M., et al., "Betulinic Acid Derivatives: A New Class of Human Immunodeficiency Virus Type 1 Specific Inhibitors with a New Mode of Action", (1996) J. Med. Chem., vol. 39, p. 1056-1068.

Kashiwada et al., *Anti-AIDS Agents. 30. Anti-HIV Activity of Oleanolic Acid, Pomolic Acid, and Structurally Related Triterpenoids*, J. Nat. Prod. 61:1090-1095 (1998).

Kim et al., *Synthesis of Betulinic Acid Derivatives with Activity Against Human Melanoma*, Bioorganic & Medicinal Chemistry Letters 8:1707-1712 (1998).

Pisha et al., *Discovery of Betulinic Acid as a Selective Inhibitor of Human Melanoma that Functions by Induction of Apoptosis*, 1(10):1046-1051 (1995).

Web page Sheet for KID-CALM, Internet search: 1 pg. (Jan. 31, 2002).

* cited by examiner

ANXIOLYTIC MARCGRAVIACEAE COMPOSITIONS CONTAINING BETULINIC ACID, BETULINIC ACID DERIVATIVES, AND METHODS

FIELD OF THE INVENTION

The invention relates to betulinic-acid containing extracts of the plant family Marcgraviaceae, compositions containing betulinic acid or betulinic acid derivatives, and methods for preventing or treating anxiety using same.

BACKGROUND OF THE INVENTION

There is ever-increasing interest in herbal or natural-source remedies or medications. Many individuals would rather use such products than conventional pharmaceutical preparations. Additionally, medicinal substances derived from natural products can provide commercial or industrial opportunities for local populations in areas where medicinal plants grow or are cultivated. Moreover, compounds identified as the active ingredients in natural products form an important basis for pharmaceutical research.

Anxiety is a serious disorder that affects many people. Anxiety disorders can be classified into the following sub-categories: generalized anxiety disorder, panic disorders, phobias, obsessive-compulsive disorders, posttraumatic stress disorder, acute stress disorders and anxiety disorders due to medical conditions, substance abuse and not otherwise specified anxiety (American Psychiatric Association. (1994). *Diagnostic and statistical manual of mental disorders*, 4$^{th}$ *Edn.* (*DSM-IV*). Washington, D.C.). Anxiety disorders are characterized by three basic components; subjective psychological reports, behavioural responses and physiological responses. A person usually reports subjective feelings of tension, apprehension, dread and expectations of an inability to cope (Alloy, L. B., Jacobson, N. S, & Acocella, J., (1999). *Abnormal Psychology: Current Perspectives* (pp. 150-172.). McGraw-Hill, Boston Mass.). These feelings can lead the person to behavioural responses as coping mechanisms, such as avoidance of the feared situation, impaired speech and motor functioning, and impaired performance on complex cognitive tasks. Physiological changes are often manifested as well; these include muscle tension, increased heart rate and blood pressure, dry mouth, nausea and dizziness (Weiss, S. R. B, & Uhde, T. W. (1990). Animal models of anxiety. In *Neurobiology of Panic Disorder* (pp. 3-27). Maryland: Alan R. Liss, Inc.). A natural product, or a pharmaceutical preparation derived from a natural product, would be of great interest in the alleviation of anxiety.

Marcgraviaceae is a plant family common in Costa Rica. Although the use of herbal or plant-based remedies is common throughout South America, to our knowledge, anxiolytic activity of plants of the family Marcgraviaceae, or of extracts or compounds obtained therefrom, has not been reported.

A variety of natural or herbal remedies containing betulinic acid have been described as being useful for treating depression or stress, disorders that differ from anxiety.

For instance, U.S. Pat. No. 5,589,182 to Pater and Tashiro describes a pharmaceutical composition in unit dosage form for treating various diseases including depression. The composition comprises a mixture of aqueous extracts of a number of plants, including extracts of dried seeds of *Zizyphus jujuba* containing betulinic acid. The compositions can be in the form of a health drink, in which the dried powder or concentrated aqueous solution is mixed with a syrup formula, and carbonated water is added.

The WPI abstract for Japanese Patent No. 57031620 indicates that the patent is directed to the preparation of a sweet to reduce stress when stopping smoking. The sweet is prepared by boiling seeds of gardenia in water, boiling persimmon leaves in water, and then mixing the two solutions with corn syrup. The abstract indicates that the solution of boiled persimmon leaves contains, among other things, betulinic acid. The abstract provides that a dose of about 10 grains per day of the sweet can alleviate stress associated with smoking cessation.

The WPI abstract for Japanese Patent No. 69031593 appears to be directed to a method for preparation of "betulin acid" involving extracting the seeds of *Zizyphus vulgaris* var. spinosus. The abstract provides that betulin acid is a narcotic with no side effects, and is usually obtained from *Betula alba*.

Betulinic acid and various derivatives thereof are known to have pharmacological activity, and the patent literature describes the use of such compounds for the treatment of a range of conditions. However, these generally relate to disorders other than anxiety.

For instance, the use of betulinic acid and derivatives thereof for cancer chemoprevention and chemotherapy is described in U.S. Pat. No. 6,048,847 to Jaggi et al., U.S. Pat. No. 6,046,231 to Kosmeder et al., U.S. Pat. Nos. 5,869,535 and 5,658,947 to Dasgupta et al., among others.

Betulinic acid and various derivatives have also been identified as being useful as anti-viral agents. German patent application 19713768 to Draeger et al. discloses a preparation of betulinic acid for use as an anti-cancer and anti-HIV agent. U.S. Pat. No. 5,679,828 also discloses betulinic acid derivatives having anti-retroviral activity, particularly anti-HIV activity.

U.S. Pat. No. 6,124,362 to Bailey et al. identifies betulinic acid as a preferred agent in a composition for regulating hair growth, when applied topically to the scalp.

U.S. Pat. No. 5,529,769 to Cho et al. describes compositions containing betulinic acid said to be useful for the treatment of skin conditions such as wrinkling and photodamage.

Japanese Patent No. 2000-247993 appears to describe a class of triterpenoid compounds including oleanonic acid, oleanic acid, 3-epi-oleanolic acid, betulonic acid and 3-epi-betulinic acid, and indicates that some of these compounds are sigma receptor agonists. The patent appears to conclude that these compounds are therefore useful for the treatment of a broad range of disorders said to be related to the sigma receptor, such as schizophrenia, depression, worry, cerebrovascular disorder, senile activity, Alzheimer's disease, Parkinson's disease, Huntington's disease, drug addiction, stress, anxiety, depression, etc. But no data is presented that the mentioned triterpenoid compounds have any of the recited utilities, let alone anxiolytic activity.

SUMMARY OF THE INVENTION

It has now been discovered that preparations obtained from plants of the family Marcgraviaceae, particularly of the genus *Souroubea* or *Schwartzia* have potent anxiolytic activity. Betulinic acid has been determined to be the active ingredient in these preparations having anxiolytic activity.

Betulinic acid is a colorless crystalline solid forming plate-like or needle-like crystals. It has a molecular weight of 456.71, a melting point of 316-318° C., and an empirical formula of $C_{30}H_{50}O_2$. Betulinic acid is soluble in water, ethanol, ether, acetone, benzene, and chloroform. Betulic acid is a synonym for betulinic acid. The structural formula of betulinic acid is:

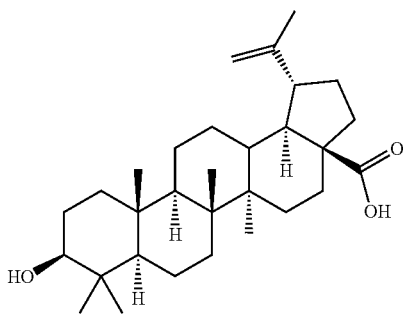

(I)

Phytochemical principles are conserved in closely related species, and all members of the family Marcgraviaceae are useful in the context of the invention. Preferred members of the family Marcgraviaceae include plants of genera *Souroubea, Schwartzia, Marcgraviastrum, Norantea, Ruyschia*, and *Sarcopera*. Particularly preferred are plants of the genera *Souroubea* and *Schwartzia*. Especially preferred are plants of the genus *Souroubea*. A preferred *Souroubea* species is *Souroubea sympelata* Gigli (synonyms *Souroubea guianensis* Aubl.; *Ruyschia quianensis* (Aubl.) Sw.). *S. sympetala* is a Neotropical vine that is indigenous to Guatemala, Belize, Nicaragua, Costa Rica, Panama, Colombia, Venezuela, and Peru. Another exemplary *Souroubea* species is *S. gilgii* V.A. Richt (synonym *Souroubea belizensis* Lundell), a Mesoamerican vine indigenous to Guatemala, Belize, Nicaragua, Costa Rica, and Panama. Other preferred *Souroubea* species include, without limitation, *S. loczyi* de Roon, *S. venosa* Shery, and *S. vallicola* Woodson.

Thus, in one aspect, the invention provides a betulinic acid-containing preparation obtained from a plant of the family Marcgraviaceae. As used herein and in the claims, a "preparation" obtained from Marcgraviaceae means a non-naturally occurring composition of matter that contains less than the entire complement of biological materials found in the entire plant or plant part. In this respect, an intact or ground-up fruit of Marcgraviaceae would not constitute a "preparation" as defined herein, but a composition from which some or all of the moisture, fibre or carbohydrates are separated, would constitute a "preparation." A wide range of preparations is contemplated. For instance, a betulinic-acid containing tea-like beverage, made by steeping *Souroubea* leaves in hot water, and then removing the leaves, would constitute a preparation as defined herein. Similarly, a dried, finely ground powder of Marcgraviaceae leaves would constitute a "preparation," as the powder would have a moisture content far below that found in nature.

Preferably, the Marcgraviaceae preparation is an extract obtained by contacting Marcgraviaceae plant material, such as fruit, leaves, other plant parts, or a mixture thereof, with a solvent in which betulinic acid is soluble, to form a betulinic acid-containing extract, and then recovering the betulinic acid-containing extract, as exemplified in the Examples herein. Preferably, the solvent used is other than water.

As used herein and in the claims, the term "plant" encompasses whole plants as well as plant parts, including, without limitation, plant cells, tissues, seeds, embryos, roots, leaves, stems, et cetera.

The preparation may take the form of a pharmaceutical composition for preventing or treating anxiety, comprising a preparation as described above together with one or more pharmaceutically acceptable carriers, diluents, or excipients, as are known in the art.

In another aspect, the invention provides a commercial package comprising a betulinic acid-containing preparation obtained from a plant of the family Marcgraviaceae, and instructions for use of said preparation for preventing or treating anxiety in a subject.

The invention also provides a method for making an anxiolytic extract of Marcgraviaceae, comprising the steps of:

(a) contacting a Marcgraviaceae plant or a part thereof, with a solvent in which betulinic acid is soluble, to form a betulinic acid-containing extract; and, (b) recovering said extract.

As discussed above, the solvent used is preferably other than water.

The invention further provides a method for preventing or treating anxiety in a subject comprising administering to a subject in need thereof a therapeutically effective amount of a betulinic acid-containing preparation obtained from Marcgraviaceae.

In another aspect, the invention extends to the use of a plant of the family Marcgraviaceae for the prevention or treatment of anxiety in a subject.

The invention further extends to the use of a plant of the family Marcgraviaceae for the manufacture of an anxiolytic preparation.

In another aspect, the invention provides a method for preventing or treating anxiety in a subject comprising administering to a subject in need thereof a therapeutically effective amount of betulinic acid, or a pharmaceutically acceptable salt thereof.

In another aspect, the invention provides a pharmaceutical composition for preventing or treating anxiety in a subject comprising a therapeutically effective amount of betulinic acid, or a pharmaceutically acceptable salt thereof, and a pharmaceutically acceptable carrier, diluent, or excipient.

In another aspect, the invention contemplates use of betulinic acid, or a pharmaceutically acceptable salt thereof for the prevention or treatment of anxiety in a subject.

In another aspect, the invention contemplates use of betulinic acid, or a pharmaceutically acceptable salt thereof, for the manufacture of a medicament for the prevention or treatment of anxiety.

In yet another aspect, the invention provides a commercial package comprising betulinic acid, or a pharmaceutically acceptable salt thereof, and instructions for use for preventing or treating anxiety.

It has further been discovered that, surprisingly, a range of derivatives of betulinic acid have potent anxiolytic activity. These compounds are of the formula:

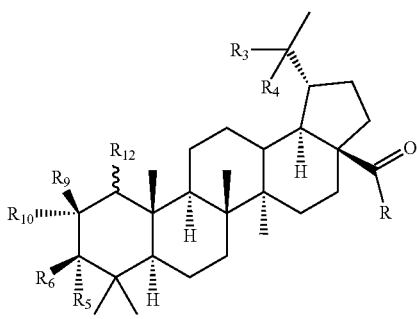

or pharmaceutically acceptable salts thereof, wherein R is H, OH, unsubstituted or substituted $C_1$-$C_6$ alkoxy, unsubstituted or substituted $C_2$-$C_6$ alkenyloxy, unsubstituted or substituted $C_2$-$C_6$ alkynyloxy, unsubstituted or substituted $C_1$-$C_3$ alkyloxy(aryl), unsubstituted or substituted $C_1$-$C_3$ alkyloxy(heteroaryl) containing up to two heteroatoms selected from the group consisting of N, O and S, unsubstituted or substituted aryloxy, an unsubstituted or substituted 5- or 6-membered heteroaryloxy ring system containing up to two heteroatoms selected from the group consisting of N, O and S; or R is

wherein $R_1$ and $R_2$ are, independently, H, OH, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_3$ alkyl(aryl), unsubstituted or substituted aryl, or wherein $R_1$ and $R_2$, together with the nitrogen atom to which they are bonded, form a residue of an amino acid or an alkyl ester of a residue of an amino acid, or wherein $R_1$ and $R_2$, together with the nitrogen atom to which they are bonded form an unsubstituted or substituted three to seven membered ring possibly containing an additional heteroatom selected from the group consisting of N, O and S;

$R_3$ and $R_4$ taken together form =$CH_2$, =$CHR_8$, =O, —$OCH_2$—, or $R_3$ is H or OH and $R_4$ is H, OH, $CH_2OH$, unsubstituted or substituted $C_1$-$C_6$ alkyl, unsubstituted or substituted aryl, unsubstituted or substituted heteroaryl containing up to two heteroatoms selected from the group consisting of N, O and S, $CH_2$—$R_7$ or $NR_1R_2$, wherein $R_7$ is a ketone, sulfoxide, sulfone, ester or nitrile, and wherein $R_1$ and $R_2$ are as defined above, and wherein $R_8$ is defined as for $R_4$ except that $R_8$ is not H or OH $R_5$ and $R_6$ taken together form =O, or, $R_5$ is H and $R_6$ is OH,

($C_1$-$C_6$ alkyl), unsubstituted or substituted $C_1$-$C_6$ alkoxy, or $R_6$ is

where $R_1$ and $R_2$ are as defined above;

$R_9$ and $R_{10}$ are, independently, H, OH, $CH_2$—$R_{11}$, a halogen, $SCH_3$, $S(O)CH_3$, $SO_2CH_3$, unsubstituted or substituted S-aryl, unsubstituted or substituted S(O)-aryl, unsubstituted or substituted $SO_2$-aryl, unsubstituted or substituted S-heteroaryl containing up to two heteroatoms selected from the group consisting of N, O and S, unsubstituted or substituted S(O)-heteroaryl containing up to two heteroatoms selected from the group consisting of N, O and S, unsubstituted or substituted $SO_2$-heteroaryl containing up to two heteroatoms selected from the group consisting of N, O and S, with the proviso that $R_9$ and $R_{10}$ cannot both be OH, wherein $R_{11}$ is H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl or unsubstituted or substituted heteroaryl containing up to two heteroatoms selected from the group consisting of N, O and S;

$R_{12}$ is H, or $R_9$ or $R_{10}$, together with $R_{12}$ form a bond.

Therefore, in a further aspect, the invention provides a method for preventing or treating anxiety in a subject comprising administering to a subject in need thereof a therapeutically effective amount of a compound of formula II as defined above.

In another aspect, the invention also contemplates use of a compound of formula II as defined above for preventing or treating anxiety, as well as use of such compounds for the manufacture of a medicament for the treatment or prevention of anxiety.

In yet another aspect, the invention provides a commercial package comprising a compound of formula II as defined above, and instructions for use of the compound for treating or preventing anxiety in a subject.

When used in accordance with the invention, the active ingredient is preferably provided in the form of a pharmaceutical composition comprising a compound as described above together with one or more pharmaceutically acceptable carriers, diluents, or excipients, as are known in the art. Additional active ingredients, such as additional anxiolytic agents, as are known in the art, may also be present.

DETAILED DESCRIPTION OF THE INVENTION

Marcgraviaceae Preparations

Figure 1:
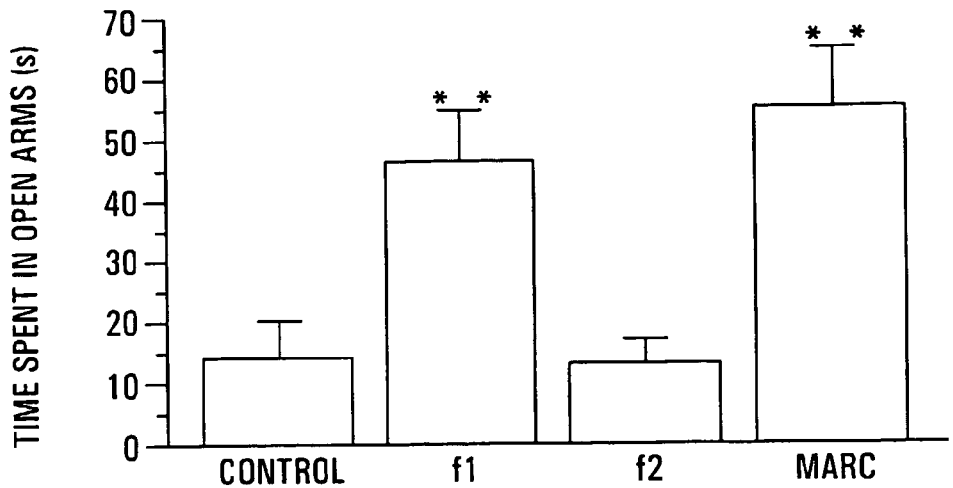
FIG. 1 is a bar graph depicting the time spent (seconds) in the open arms of an elevated plus-maze by animals administered sweetened milk (control), 95% ethanol crude Marcgraviaceae plant extract (marc.), ethyl acetate fraction (f1) and aqueous fraction (f2) (**Significantly different from control at p<0.01).

Betulinic acid-containing preparations of Marcgraviaceae may be prepared by, for instance, blending or macerating Marcgraviaceae leaves, fruit, or other plant parts in a solvent in which betulinic acid is soluble, filtering the blended material, and then evaporating the solvent. Suitable solvents include, without limitation, water, ethyl acetate, dichloromethane, or low molecular weight alcohols such as methanol, ethanol, propanol, or butanol. A solvent other than water is generally preferred. The resulting preparation may take the form of a solid (such as a powder), a liquid, or other forms. Alternatively, a preparation of Marcgraviaceae can be prepared by drying Marcgraviaceae plants or plant parts, and then reducing the dried materials to a powder. In an exemplified case, the extract is a dark, viscous oil, which contains betulinic acid.

The preparation can be concentrated to varying degrees, limited principally by the amount of plant material a patient can conveniently ingest. Generally, at least the fibrous plant material and naturally-occurring plant carbohydrates are separated. Typically, the preparation will contain betulinic acid in an amount of at least 0.1% to 90% by weight, based on the Marcgraviaceae-derived portion of the preparation, and preferably contains at least 0.5%, more preferably at least 1%, even more preferably at least 2%, 3%, 4%, 5%, 10%, 15%, 20%, 30%, 40%, 50%, 60%, 70% or 80% by weight betulinic acid, based on the Marcgraviaceae derived portion of the preparation.

The Marcgraviaceae preparation may be incorporated into a pharmaceutical composition (as discussed herein), or into a supplement, such as a nutritional supplement, a food product, a beverage, or the like, as known in the art.

Betulinic Acid and Betulinic Acid Derivatives

The invention also provides pharmaceutical compositions for treating or preventing anxiety, comprising betulinic acids or betulinic acid derivatives as defined herein.

As employed herein, the singular forms "a," "an," and "the" include plural reference unless the context clearly dictates otherwise.

As employed herein, "alkyl" refers to straight or branched, cyclic or non-cyclic chain alkyl; "substituted alkyl" refers to alkyl radicals further bearing one or more substituents such as hydroxy, alkoxy (of an alkyl group), mercapto (of an alkyl group), aryl, heteroaryl, heterocyclic, halogen, trifluoromethyl, cyano, nitro, amino, carboxyl, carboxyalkyl, carbamate, sulfonyl, sulfonamide, and the like;

"alkenyl" refers to straight or branched, cyclic or non-cyclic hydrocarbyl chain radicals having at least one carbon-carbon double bond; "substituted alkenyl" refers to alkenyl radicals further bearing one or more substituents as set forth above;

"alkynyl" refers to straight or branched, cyclic or non-cyclic hydrocarbyl chain radicals having at least one carbon-carbon triple bond; "substituted alkynyl" refers to alkynyl radicals further bearing one or more substituents as set forth above;

"aryl" refers to aromatic radicals having in the range of 6 to 14 carbon atoms; "substituted aryl" refers to aryl radicals further bearing one or more substituents as set forth above;

"heteroaryl" refers to aromatic radicals having in the range of 6 to 14 carbon atoms containing one or more heteroatoms (e.g., N, O, S, or the like) as part of the ring structure; "substituted heteroaryl" refers to heteroaryl radicals further bearing one or more substituents as set forth above;

"alkoxy" refers to straight or branched, cyclic or non-cyclic, alkyl chains comprising an oxy radical group; "substituted alkoxy" refers to alkoxy radicals further bearing one or more substituents as set forth above;

"alkenyloxy" refers to straight or branched, cyclic or non-cyclic, hydrocarbyl chains having at least one carbon-carbon double bond and comprising an oxy radical group; "substituted alkenyloxy" refers to alkenyloxy radicals further bearing one or more substituents as set forth above;

"alkynyloxy" refers to straight or branched, cyclic or non-cyclic, hydrocarbyl chains having at least one carbon-carbon triple bond and comprising an oxy radical group; "substituted alkynyloxy" refers to alkynyloxy radicals further bearing one or more substituents as set forth above;

"aryloxy" refers to aromatic hydrocarbyls having in the range of 6 to 14 carbon atoms and comprising an oxy radical group; "substituted aryloxy" refers to aryloxy radicals further bearing one or more substituents as set forth above;

"heteroaryloxy" refers to aromatic hydrocarbyls having in the range of 6 to 14 carbon atoms containing one or more heteroatoms (e.g., N, O, S, or the like) as part of the ring structure and comprising an oxy radical group; "substituted heteroaryloxy" refers to heteroaryloxy radicals further bearing one or more substituents as set forth above;

"alkyl(aryl)" refers to aryl-substituted alkyl radicals; "substituted alkyl(aryl)" refers to alkyl(aryl) radicals further bearing one or more substituents as set forth above;

"alkyl(heteroaryl)" refers to heteroaryl-substituted alkyl radicals; "substituted alkyl(heteroarylaryl)" refers to alkyl (heteroaryl) radicals further bearing one or more substituents as set forth above;

"alkyloxy(aryl)" refers to aryl-substituted alkyl chains comprising an oxy radical group; "substituted alkyloxy(aryl)" refers to alkyloxy(aryl) radicals further bearing one or more substituents as set forth above;

"alkyloxy(heteroaryl)" refers to heteroaryl-substituted alkyl chains comprising an oxy radical group; "substituted alkyloxy(heteroaryl)" refers to alkyloxy(heteroaryl) radicals further bearing one or more substituents as set forth above;

Preferred compounds of the Formula II are those in which R is unsubstituted or substituted $C_1$-$C_6$ alkoxy or $NR_1R_2$. Preferred for $R_1$ and $R_2$ are H, unsubstituted or substituted $C_1$-$C_6$ alkyl, unsubstituted or substituted C1-C3 alkyl(aryl), unsubstituted or substituted aryl, an unsubstituted or substituted $C_3$ to $C_7$ ring when taken together with the nitrogen atom to which they are bonded, or an amino acid residue such as glycine. Preferred values for $R_3$ and $R_4$ are H or, when taken together, is =$CH_2$. Preferred for $R_5$ is H; for $R_6$ is OH or O—C(O)—($C_1$-$C_6$ alkyl); or $R_5$ and $R_6$ taken together are =O. Preferred values for $R_9$, $R_{10}$, and $R_{12}$ are H. Betulonic acid may be excluded from the list of preferred derivatives. The compound of the Formula II wherein R is OH, $R_3$ and $R_4$ when taken together are =$CH_2$, $R_5$ is H, $R_6$ is OH and $R_9$, $R_{10}$ and $R_{12}$ are H represents betulinic acid itself, and is also excluded from the list of preferred derivatives.

Derivatives of betulinic acid that are also encompassed by the Formula II may be synthesized using procedures generally known in the art. Thus, for example, compounds of the Formula II wherein R is H may be prepared by the reduction of the corresponding acid to the aldehyde. Compounds of the Formula II in which R is alkoxy, alkenyloxy, alkynyloxy, aryloxy or heteroaryloxy may be prepared, for example, by esterification of the acid moiety of an appropriate betulinic acid derivative. For example esters are produced by reacting an alkali metal salt of the acid with alkyl chloride or bromide in THF in the presence of a catalytic amount of tetrabutylammonium iodide. Alkyl tosylates may also be employed.

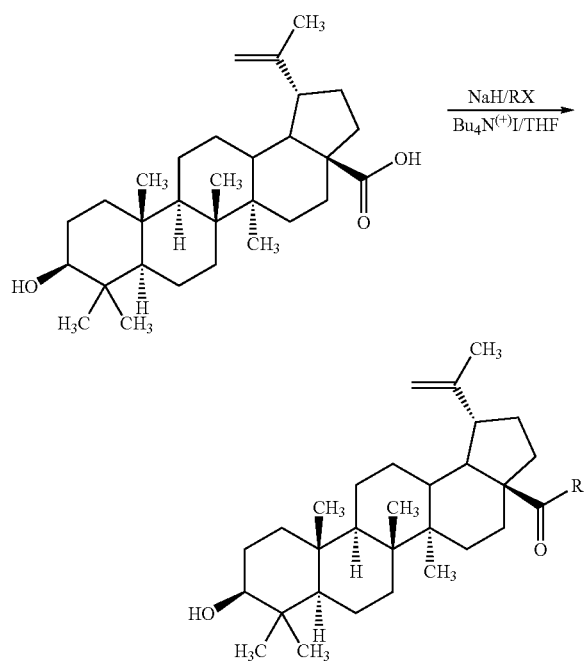

The methyl ester of betulinic acid derivatives can be obtained from the corresponding acid by reaction with diazomethane in diethyl ether. Surprisingly, the well-known conversion of carboxylic acids into esters by reaction of the acid with an alcohol in the presence of a mineral acid does not work well for the conversion of betulinic acid into its alkyl, alkyl(aryl) or alkyl(heteroaryl) esters.

Compounds of the Formula II in which R is $NR_1R_2$ may be prepared, for example, by the amidation of the acid moiety of an appropriate betulonic acid derivative. An example is the conversion of betulonic acid to N-benzyl betulinic acid amide. Betulonic acid is converted to its acid chloride upon reaction with $SOCl_2$ or $POCl_3$, reacted with benzylamine to generate the amide function. Finally, the 3-keto function is reduced to the 3-β-ol with $NaBH_4$ in methanol. This approach can also be used to prepare ester simply by replacing the amine with an alcohol and an equivalent of triethylamine.

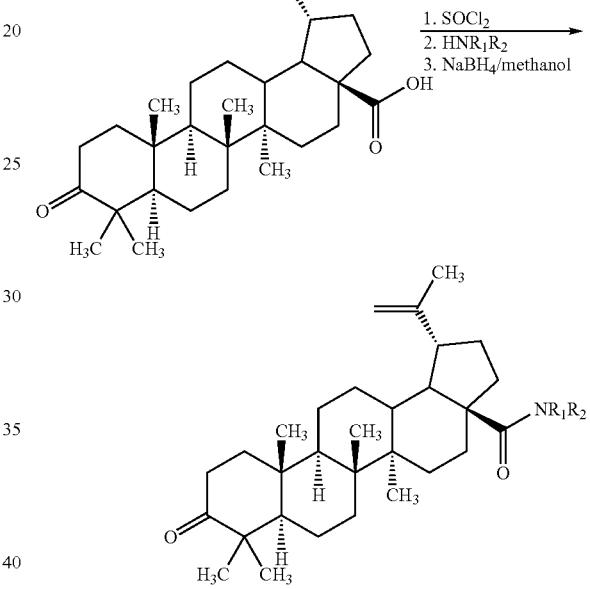

Derivatives in which R=OH and $R_6$ is alkoxy or acyloxy can also be converted into the corresponding esters, R=OR, and amides, R=$NR_1R_2$, by reaction conversion to the acid chloride (R=Cl) followed by treatment with alcohols and triethylamine and prepared by reacting the compound having R=OR and R=$NR_1R_2$ with the appropriate acyl derivatives in the presence of pyridine and DMAP.

Compounds of the Formula II in which $R_3$ and $R_4$ are hydrogen may be prepared, for example, from the hydrogenation of the alkene moiety of an appropriate betulinic acid derivative. Compounds of the Formula II in which $R_3$ and $R_4$ when taken together are =O may be prepared, for example, from the ozonolysis of the corresponding alkene. Reduction of this ozonolysis product would yield compounds of the Formula II in which $R_3$ is hydrogen and $R_4$ is OH. Reaction of the ozonolysis product with an appropriate Grignard or organolithium reagent could provide compounds of the Formula II in which $R_3$ is OH and $R_4$ is unsubstituted or substituted alkyl, cycloalkyl, aryl (such as phenyl) or heteroaryl (such as thiophenyl or furanyl). Acid catalyzed dehydration of compounds wherein $R_3$ is OH and $R_4$ is a group other than H, OH or $CH_2OH$ would result in compounds in which $R_4$ is =$CHR_8$. The reaction of $LiCH_2EWG$ (wherein EWG is an electron withdrawing group such as a ketone, sulfoxide, sulfone, ester or nitrile) with a betulinic acid derivative in which $R_3$ and $R_4$ when taken together are =O may be used to yield compounds of the Formula II in which $R_3$ is hydrogen and $R_4$ is $CH_2EWG$. The reaction of a betulinic acid derivative in which $R_3$ and $R_4$ when taken together are =O with ammonia, or with an appropriate primary or secondary amine or with an appropriate amino acid under slightly acidic conditions and reduction of the resulting immonium ion or imine with a suitable reducing agent such as $NaBH_3CN$ leads to compound in which $R_3$ is H and $R_4$ is $NH_2$, or the substituents on the amine employed in the reaction minus a H bonded to N.

Appropriate betulonic acid derivatives can be converted into the 3-β-amino derivatives, $R_5$=H, $R_6$=$NR_1R_2$, via the reductive amination technique in which the 3-keto function is reacted with a primary or secondary amine under mildly acidic conditions in the presence of $NaBH_3CN$.

betulinic acid derivative. The 3-OH moiety may also be etherified by known methods. Derivatives in which the C2 substituents have been modified to give the designated $R_9$, and/or $R_{10}$, can be accessed by reacting the appropriate betulonic acid derivative with lithium di-isopropylamide in RHF at low temperature and quenching the intermediate enolate with a variety of electrophiles. Potential electrophiles include alkyl or substituted alkyl bromides, iodides or sulfonates esters, dialkyl disulfides, diaryl disulfides, halogens or pseudohalogens, electrophilic oxygen species such as oxaziridines. The 2-thioether derivatives can be oxidized to the corresponding sulfoxides or sulfones with one or two equivalents or oxidizing agents such as meta-chloroperbenzoic acid.

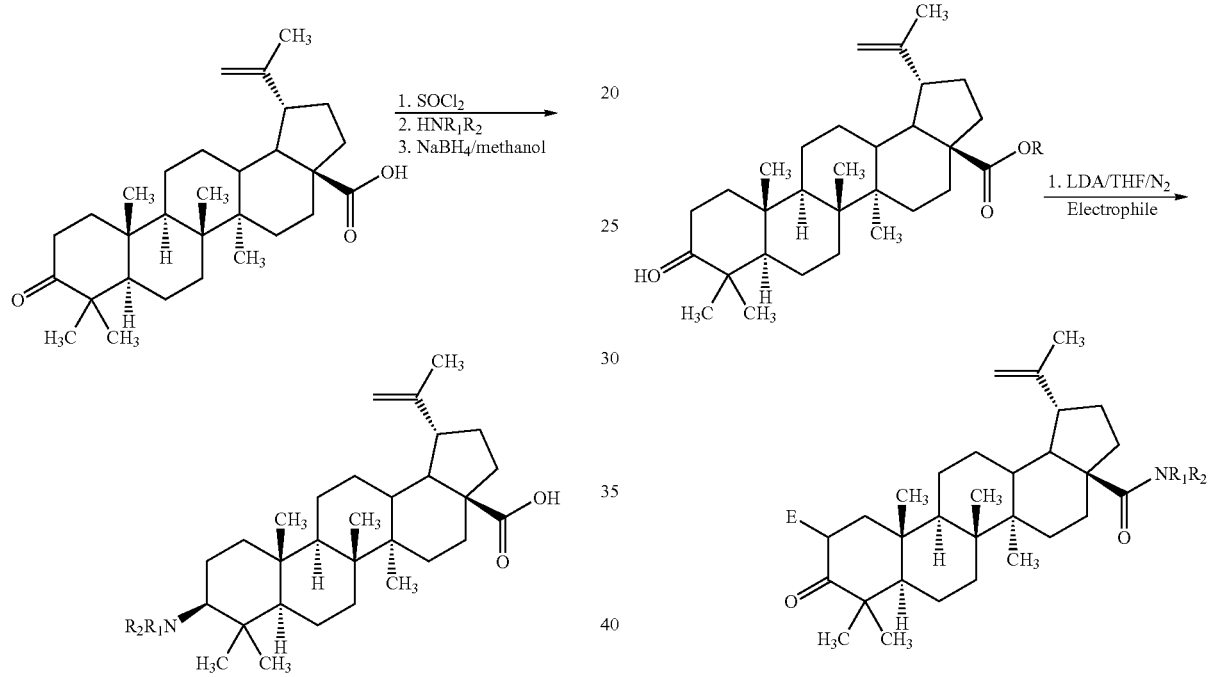

The alkene moiety of an appropriate betulinic acid derivative may be epoxidized with peracids to form compounds in which $R_3$ and $R_4$ form —O($CH_2$)—, or, may be subjected to hydroboration to form compounds in which $R_3$ is H and $R_4$ is $CH_2OH$.

Compounds of the Formula II in which $R_6$ is an ester may be formed by esterifying the 3-OH moiety of an appropriate β-Keto sufoxides can be converted into α,β-unsaturated ketones by heating to approximately 110° C. This leads to compounds in which $R_{12}$ and $R_9$ or $R_{10}$ are taken together to form a bond or, in other words, compounds that have a double bond between C1 and C2.

Table 1 illustrates some betulinic acid derivatives that may be prepared in accordance with the invention.

TABLE 1

| # | Name | R | $R_1$ | $R_2$ | $R_3$ | $R_4$ | $R_5$ | $R_6$ |
|---|------|---|-------|-------|-------|-------|-------|-------|
| 1 | Betulinic acid (BA) | OH | — | — | | =$CH_2$ | H | OH |
| 2 | Betulonic acid | OH | — | — | | =$CH_2$ | | =O |
| 3 | Methyl dihydrobetulinate | $OCH_3$ | — | — | H | H | H | OH |
| 4 | 3-acetoxyBA | OH | — | — | | =$CH_2$ | H | $CO_2CH_3$ |
| 5 | Methyl betulinate | $OCH_3$ | — | — | | =$CH_2$ | H | OH |
| 6 | Methyl 3-acetoxybetulinate | $OCH_3$ | — | — | | =$CH_2$ | H | $CO_2CH_3$ |
| 7 | BA amide | $NR_1R_2$ | H | H | | =$CH_2$ | H | OH |
| 8 | BA benzylamide | $NR_1R_2$ | H | $CH_2Ph$ | | =$CH_2$ | H | OH |
| 9 | BA anilide | $NR_1R_2$ | H | Ph | | =$CH_2$ | H | OH |
| 10 | BA pyrrolidine amide | $NR_1R_2$ | | —($CH_2$)$_4$— | | =$CH_2$ | H | OH |

TABLE 1-continued

| # | Name | R | $R_1$ | $R_2$ | $R_3$ | $R_4$ | $R_5$ | $R_6$ |
|---|---|---|---|---|---|---|---|---|
| 11 | Betulonic acid isobutyl amide | $NR_1R_2$ | H | $CH_2CH(CH_3)_2$ | | $=CH_2$ | | $=O$ |
| 12 | BA isobutyl amide | $NR_1R_2$ | H | $CH_2CH(CH_3)_2$ | | $=CH_2$ | H | OH |
| 13 | BA glycine methyl ester amide | $NR_1R_2$ | H | $CH_2CO_2CH_3$ | | $=CH_2$ | H | OH |
| 14 | BA glycine amide | $NR_1R_2$ | H | $CH_2CO_2H$ | | $=CH_2$ | H | OH |
| 15 | DihydroBA | OH | — | — | H | H | H | OH |
| 16 | Ethyl betulinate | $OCH_2CH_3$ | — | — | | $=CH_2$ | H | OH |
| 17 | 3-acetoxy betulinic acid hydroxylamine | $NR_1R_2$ | H | OH | | $=CH_2$ | H | $O(CO)CH_3$ |
| 18 | See table II | OH | — | — | | $=O$ | H | OH |
| 19 | See table II | OH | — | — | | $=O$ | H | $O(CO)CH_3$ |
| 20 | See table II | $-OCH_3$ | — | — | H | OH | H | OH |
| 21 | See table II | $NR_1R_2$ | H | $CH_2Ph$ | | $=O$ | H | $O(CO)CH_3$ |
| 22 | See table II | $-OCH_3$ | — | — | | $=O$ | H | $O(CO)CH_3$ |
| 23 | See table II | $-OCH_3$ | — | — | H | $CH_2OH$ | H | OH |

TABLE 2

Formula of compounds 18-23 from Table 1

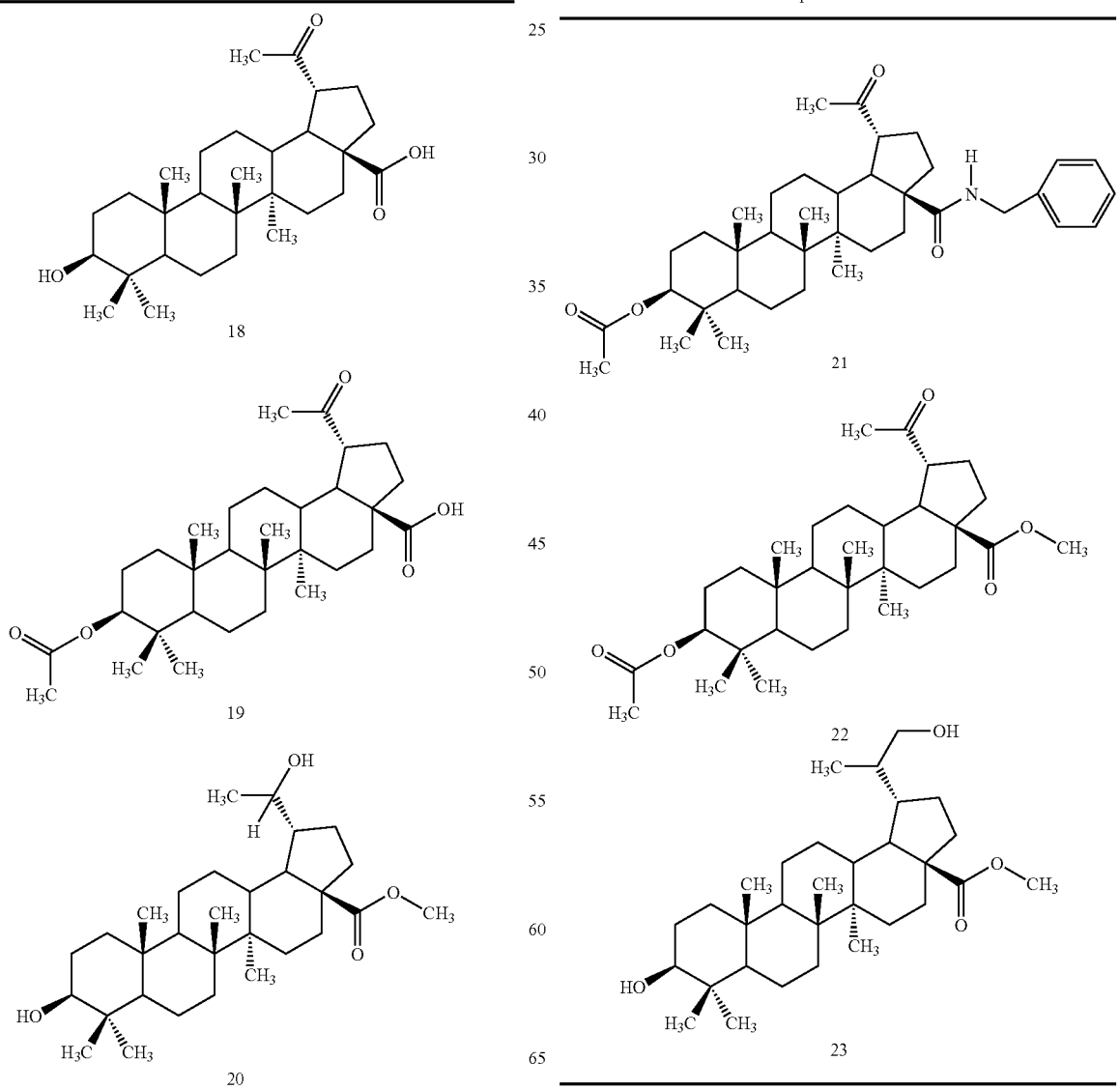

Pharmaceutical Compositions

Pharmaceutical compositions can be prepared that comprise as active ingredients: a preparation of Marcgraviaceae; betulinic acid in free form or in the form of a pharmaceutically acceptable salt; or a compound of formula II in free form or in the form of a pharmaceutically acceptable salt.

Such pharmaceutically acceptable salts are known to those skilled in the art and include, but are not limited to, sodium, potassium, lithium, calcium, magnesium, zinc and iron salts. Exemplary, but non-limiting, salts include alkali metal salts, such as sodium or potassium salts; alkaline earth metal salts, such as calcium or magnesium salts; ammonium or alkylammonium salts, wherein the alkylammonium cation has one to three alkyl groups and each alkyl group independently has one to four carbon atoms; or transition metal salts.

These pharmaceutical compositions are compositions for enteral (e.g. oral) administration, and also rectal or parenteral administration, also for topical administration to warm-blooded animals (particularly humans), the pharmacological active ingredient being present alone or together with customary pharmaceutical excipients.

The pharmaceutical compositions comprise, for example, approximately from 0.1% to 100%, preferably from approximately 1% to approximately 60%, of the active ingredient. Pharmaceutical compositions for enteral or parenteral administration are, for example, in unit dose forms, such as dragees, tablets, capsules or suppositories, and also ampoules. They are prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture and processing the mixture of granules, if desired or necessary after the addition of suitable excipients, into tablets or dragee cores.

Suitable carriers include, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatin, gum tragacanth, methylcellulose and/or polyvinylpyrrolidone, and, if desired, disintegrators, such as the above-mentioned starches, also carboxymethyl starch, cross-linked polyvinylpyrrolidone, agar or alginic acid or a salt thereof, such as sodium alginate.

Excipients include, especially, flow conditioners and lubricants, for example silicic acid, talc, stearic acid or salts thereof, such as magnesium or calcium stearate, and/or polyethylene glycol. Dragee cores are provided with suitable coatings that may be resistant to gastric juices, there being used, inter alia, concentrated sugar solutions which may contain gum arabic, talc, polyvinylpyrrolidone, polyethylene glycol and/or titanium dioxide, coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragee coatings, for example for identification purposes or to indicate different doses of active ingredient.

Further orally administrable pharmaceutical compositions include dry-filled capsules consisting of gelatin, and also soft sealed capsules consisting of gelatin and a plasticizer, such as glycerol or sorbitol. The dry-filled capsules may contain the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

Rectally administrable pharmaceutical compositions, for example, suppositories that comprise a combination of the active ingredient and a suppository base are also provided. Suitable as suppository bases are, for example, natural or synthetic triglycerides, paraffin hydrocarbons, polyethylene glycols and higher alkanols. It is also possible to use gelatin rectal capsules that comprise a combination of the active ingredient and a base material. Suitable base materials are, for example, liquid triglycerides, polyethylene glycols and paraffin hydrocarbons.

Aqueous solutions of an active ingredient in water-soluble form, for example a water-soluble salt, are particularly suitable for parenteral administration. Also suitable for parenteral administration are suspensions of the active ingredient, such as corresponding oily injection suspensions, these being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran and optionally also stabilisers.

The dose of the active ingredient may depend on various factors, such as the method of administration, species of warm-blooded animal, age and/or individual condition. The preferred route of administration is oral administration. The active ingredient may be administered in a range of about 0.1 to about 10 mg/kg body weight per dose, more preferably about 0.1 to about 2.5 mg/kg body weight per dose, even more preferably about 0.1 to about 0.25 mg/kg body weight per dose.

The anxiolytic compounds of the present invention are fast acting (effective within 45-60 minutes after oral administration). Further, development of tolerance or desensitization to the anxiolytic compounds is low, and cessation of chronic treatment fails to elicit overt withdrawal effects. Hence, the anxiolytic compounds may be used to treat either or both of acute or chronic anxiety. For instance, treatment of a subject may involve daily or near-daily administration of the anxiolytic compounds for at least 21 days, 30 days, two months, three months, six months, one year or more.

In a normal case, the approximate estimated daily dose for a human patient weighing approximately 75 kg is, in the case of oral administration, from about 7.5 to about 750 mg.

Pharmaceutical compositions of the invention may contain betulinic acid or a betulinic acid derivative as the sole active (i.e. anxiolytic) ingredient, or may contain an additional active ingredient, e.g. an additional anxiolytic drug such as a benzodiazepine or buspirone.

The invention is further illustrated by the following non-limiting Examples.

EXAMPLE 1

This example illustrates the preparation of a *Souroubea* extract from leaves.

*Souroubea sympetala* leaves were collected at Bioforesta, Costa Rica. The leaves were immediately preserved in 95% ethanol and stored either at room temperature or in a refrigerator.

The leaves and the 95% ethanol were blended. Additional 95% ethanol was added to facilitate the blending process. The blended material was kept for 2 days at room temperature, then filtered. The dried filter cake, which is leaf fiber, weighed 178 g.

The filtrate was evaporated under reduced pressure to afford 40.1 g of a dark powder. This powder was extracted 3 times by stirring rapidly with 150 ml of ethyl acetate. The ethyl acetate extracts were combined and the solvent was evaporated to afford 8.0 g of a dark viscous oil. This oil was used in rat anti-anxiety bio-assays.

EXAMPLE 2

This example illustrates the preparation of a *Souroubea* extract from fruit.

*Souroubea sympetala* fruit was collected at Bioforesta, Costa Rica, and preserved in 95% ethanol, and was processed similarly to the *S. sympetala* leaves. The results were as follows: Dried, insoluble in 95% ethanol, 68.5 g fiber; ethanol soluble material 8.5 g; dried ethyl acetate soluble extracts 0.37 g.

EXAMPLE 3

This example illustrates the chromatographic separation of components from leaves of *Souroubea*.

The ethyl acetate soluble extracts [5.70 g] were chromatographed on 250 g of silica gel using a solvent gradient from 100:0 hexane:ethyl acetate to 0:100 hexane:ethyl acetate. One hundred fractions, each containing approximately 20 ml of eluent, were collected.

The major components were found in fractions 15-25 (1.2 g). This material was shown by spectroscopics methods to be a mixture of β-amyrin, and germanicol.

Fractions 32-50 yielded 560 mg of a solid that was rechromatographed. Two pure substances were subsequently isolated. The less polar product, 26 mg, was identified as chondrillasterol and the more polar material as betulinic acid by comparison of melting points and spectroscopic data (MS and $^1$H NMR) with known literature data. The betulinic acid content in the ethyl acetate soluble extracts of *S. sympetala* is at least 0.44%.

EXAMPLE 4

This example illustrates the chromatographic separation of components from fruit of *Souroubea*.

The ethyl acetate soluble portion of the *S. sympetala* fruit was processed as above. Betulinic acid (20 mg) was isolated from 370 mg of extracts. The betulinic acid content in this fraction is 5.4%.

EXAMPLE 5

This example illustrates that a 95% ethanol extract of leaves from *Souroubea* alleviates anxiety in the elevated plus-maze test.

The majority of tests described in the following examples were conducted on adult; male Sprague-Dawley rats (typically weighing ~300-450 gm) were obtained from Charles River Canada, St. Constant, Quebec. They were individually housed in standard clear Plexiglas cages (24×30×18 cm) and maintained on a 12 hr light/dark cycle (7:00 A.M.-7:00 P.M. light phase) in a temperature and humidity controlled room. Unless indicated otherwise, animals had free access to water and maintained on a restricted diet of 5 pellets a day of Purina Lab Chow. All experimental procedures complied with the guidelines of the Canadian Council on Animal Care and were approved by the Research Ethics Committee at the University of Ottawa.

In the elevated plus-maze (EPM) paradigm, conflict is generated by the innate drive to explore the new environment (to locate food) and the fear or aversion to open spaces and heights (vulnerable or dangerous zones). Typically rodents spend more time exploring the closed portions of the maze than the open zones of the maze. Increase in the number of entries into the open arms (anxiety generating) as compared to the closed arms (safe zones), as well as any increase the time spent in the open arms in comparison to closed arms is believed to reflect reduced anxiety (Pellow, S., et al., (1985). Validation of open:closed arm entries in an elevated plus-maze as a measure of anxiety of the rat. In *Current Protocols in Neuroscience* (pp. 8.3.6-8.3.7), John-Wiley & Sons). Animals treated with classical anxiolytic drugs, such as benzodiazepines (e.g. Valium), venture out more onto the open arms of the maze.

The EPM constitutes of a plus-shaped maze with two enclosed arms (or alleys; 50×10×40 cm) and two open arms (or planks; 50×10 cm), with a 10×10 cm central zone. The EPM was positioned at a height of 50 cm off the floor. All parts of the apparatus were made from wood, with the closed arms walled in by opaque Plexiglas. The floor was lined with coarse, black rubberized material. To avoid distractions, the EPM was surrounded by black curtain and the subjects were monitored remotely, using a closed circuit camera mounted above the set-up.

The rats were randomly assigned to each of the drug conditions. The drugs were administered intraperitoneally (i.p.) or orally (by gavage) 60 min prior to testing. Prior to placement onto the EPM, the rats were placed in an open-field box for a 5-min habituation. They were then placed in the centre of the EPM, facing one of the enclosed arms and observed remotely (via video-link relay) for 5 min. Behaviours scored included time spent in the open arms of the maze, time spent in the closed arms of the maze, number of entries into the open-arms and number of entries into the closed arm of the maze. In addition, the 'risk assessment' behaviours that included the number of unprotected head-dips (protruding the head over the edge of an open-arm while the body was on the open arm of the maze), and protected head-dips (protruding the head over the edge of the maze while the hind legs are still within the closed arms) were also scored.

In this example, rats received one of: (a) sweetened milk (control); (b) 50 mg/kg of a 95% ethanol extract of leaves from *Souroubea*; (c) 50 mg/kg of an ethanol acetate fraction of leaves from *Souroubea*; or (d) 50 mg/kg of an aqueous fraction of leaves from *Souroubea*; orally (by gavage) and were tested in the elevated plus-maze test 45-60 minutes after treatment.

As can be seen in FIG. 1, rats treated with the 95% ethanol extract (marc.) or ethanol acetate fraction (f1) of *Souroubea* spent significantly more time on the open arms of the maze (as compared to controls), indicating that this plant extract imparts anxiolytic-like effects.

Bioassay guided fractionation revealed that the 'anxiolytic' activity was contained within the ethyl acetate fraction (f1).

EXAMPLE 6

This example illustrates that a crude extract of leaves from *Souroubea* alleviates anxiety in the fear-potentiated startle paradigm.

In this anxiety/fear paradigm, rats are first trained to associate a neutral stimulus (a light) with an aversive stimulus (an electric shock to the foot). In response to a burst of an auditory stimulus (110 dB white noise burst of 500 m sec duration), rats demonstrate a reflexive startle response. However, when the acoustic stimulus is preceded by a fear cue (the light in this case), there is potentiation of their natural startle response. This potentiation of startle responses is thought to result from a classically conditioned increase in fear. Anxiolysis is inferred when there is a reduction in the magnitude of the fear-potentiated startle response.

The fear potentiated startle equipment (Med-Associates, St-Albans, Vt.) constituted (1) a pressure-sensitive platform upon which the animal is placed (in an enclosure with shock-grid floor), (2) Speakers and amplifier, to deliver acoustic stimulus, (3) Computer controlled light cue, and (4) a computerized interface to deliver the auditory and/or visual stimuli, and to record the magnitude of startle detected by the platform. The whole set up is housed in a sound attenuated and darkened chamber.

The experiment involved three phases; a training phase, a screening phase and the testing phase. In the 2-day screening phase, the rats were conditioned to associate a light cue to an electric foot-shock. Specifically, a 5 sec light cue was followed by 0.5 sec foot shock (0.67 mA) at a random inter-trial intervals ranging from 30-60 sec. Each animal received 10 trials per day, for two days. The second or screening phase involved identifying the rats that learnt to associate the light cue with the shock, which was assessed by measuring their startle response in the absence and the presence of the fear cue. Only animals that showed the fear-potentiated startle response (at least a 40% increase in the startle amplitude) were used in the next phase. In the final or test phase, rats were treated 60 min prior to testing. Animals were placed in the test chambers and presented with 10 trials of 110 dB sound bursts (inter-trial interval of 30 sec) in the absence of the light cue, and the startle response recorded. This was followed by additional 5 trials where a 5 sec light-cue preceded the 110 dB sound burst. The startle amplitudes were averaged over each of the 5 trial sessions. For statistical analyses, the second 5 trial session average (without the cue) was subtracted from the last 5-trial session (with the light cue), and this difference score analyzed using ANOVA procedure.

Rats received one of: (a) 50 mg/kg of a 95% ethanol extract of leaves from *Souroubea*; (b) 50 mg/kg of an ethanol acetate fraction of leaves from *Souroubea*; or (c) peanut oil (control); orally (by gavage) and were tested in the fear-potentiated startle paradigm 45-60 minutes after treatment.

Figure 2:
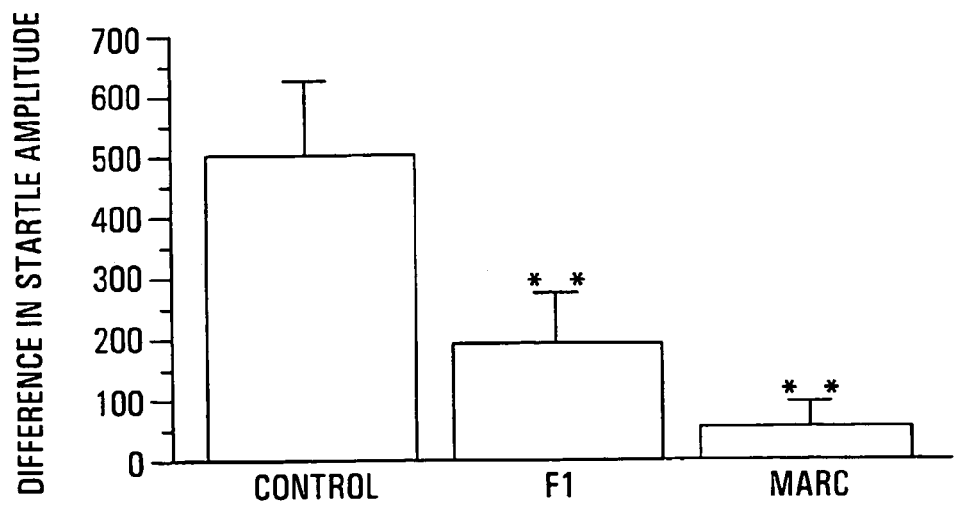
FIG. 2 is a bar graph depicting the difference in startle response (relative units) to tone presented in the absence or presence of a fear cue. Rats were administered peanut oil (control), 95% ethanol crude Marcgraviaceae plant extract (marc.), or ethyl acetate fraction (f1), prior to test (**Significantly different from control at p<0.01).

As can be seen in FIG. 2, control rats show the expected potentiation of the startle response when the light comes on, however, this response is markedly attenuated in rats pretreated with 95% ethanol extract of *Souroubea* (marc.) or the ethanol acetate fraction (F1).

Thus, the anxiolytic potential of this plant product is confirmed in two distinct and validated tests of anxiety.

EXAMPLE 7

This example illustrates that betulinic acid is the active anxiolytic ingredient of *Souroubea* as evidenced by the elevated plus-maze test.

As indicated earlier, the active ingredient(s) responsible for the anti-anxiety effects of the *Souroubea* plant, appeared to be in fraction 1 (the ethanol acetate extract).

Within this fraction, betulinic acid was identified as being present.

Rats received 1 mg/kg of betulinic acid suspended in peanut oil orally (by gavage) and were tested in the elevated plus-maze test 45-60 minutes after treatment. Control rats received only peanut oil.

Figure 3:
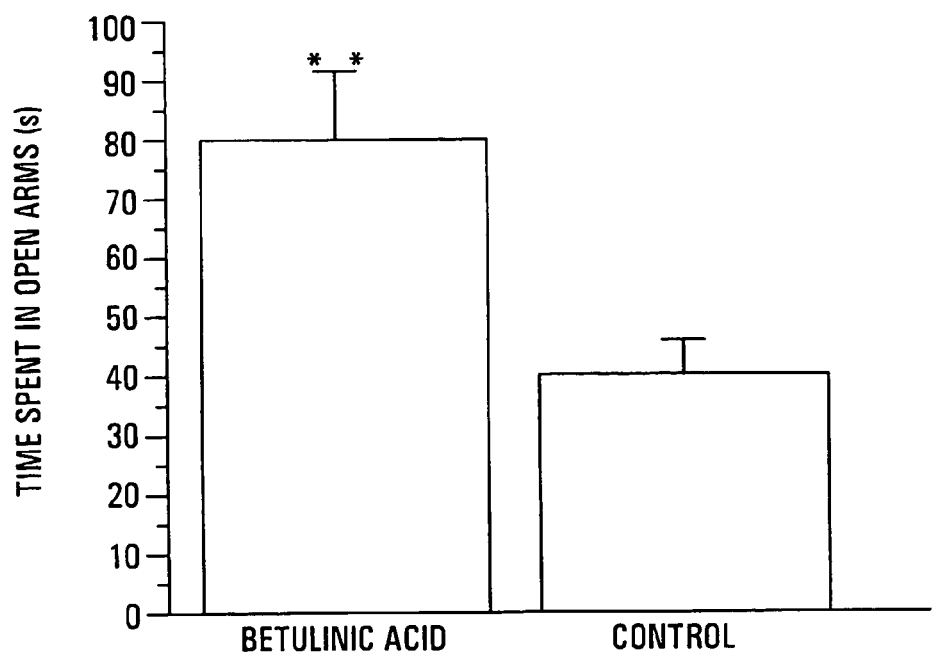
FIG. 3 is a bar graph depicting the effect of betulinic acid (1 mg/kg by gavage) on the time spent (seconds) on the open arms of the plus-maze (**Significantly different from control at $p<0.01$).

As shown in FIG. 3, rats treated with betulinic acid spent significantly more time on the open arms of the plus-maze, confirming that betulinic acid was indeed able to alleviate anxiety.

EXAMPLE 8

This example illustrates that betulinic acid has anxiolytic effects in the fear-potentiated test of anxiety.

As indicated earlier, drugs that alleviate anxiety (e.g. benzodiazepines) reduce the startle amplitude when the sound (110 dB) is presented in the presence of a cue previously paired with an aversive event (foot shock).

Rats received either: (a) 1 mg/kg betulinic acid suspended in peanut oil; or (b) peanut oil only (control); orally (by gavage) and were tested in the fear-potentiated paradigm 45-60 minutes after treatment.

Figure 4:
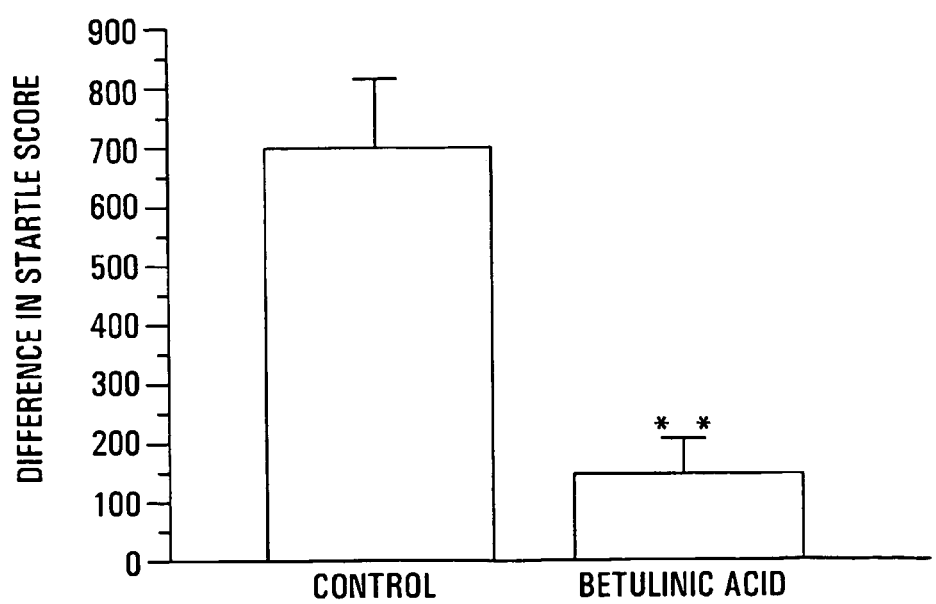
FIG. 4 is a bar graph depicting the effect of betulinic acid on fear-potentiated startle. The score reflects the difference in startle amplitude noted in the presence and absence of the fear-cue (**Significantly different from control at $p<0.01$).

As shown in FIG. 4, betulinic acid significantly attenuated the startle response in the presence of the fear-cue (but not in its absence). The scores depicted in FIG. 4 represent the difference in startle amplitude (calculated as startle response in the presence of the fear cue—startle response in the absence of the fear cue). This score was much lower in the rats pretreated with betulinic acid, suggesting that it has anti-anxiety effects.

Since the startle scores were not altered in the absence of the fear cue, one can surmise that attenuation of the fear-potentiated response is not due to non-specific motor effects.

EXAMPLE 9

This example illustrates that betulinic acid has anxiolytic effects in mice (CD-1 strain) as well.

Previous experiments were all conducted in experimental rats. Here we tested the effect of betulinic acid on CD-1 strain of mice.

Mice received 0.25 or 2.5 mg/kg of betulinic acid, or peanut oil only (control), intra peritoneally ("i.p."), and were tested 45-60 minutes later in the elevated plus maze test.

Figure 5A:
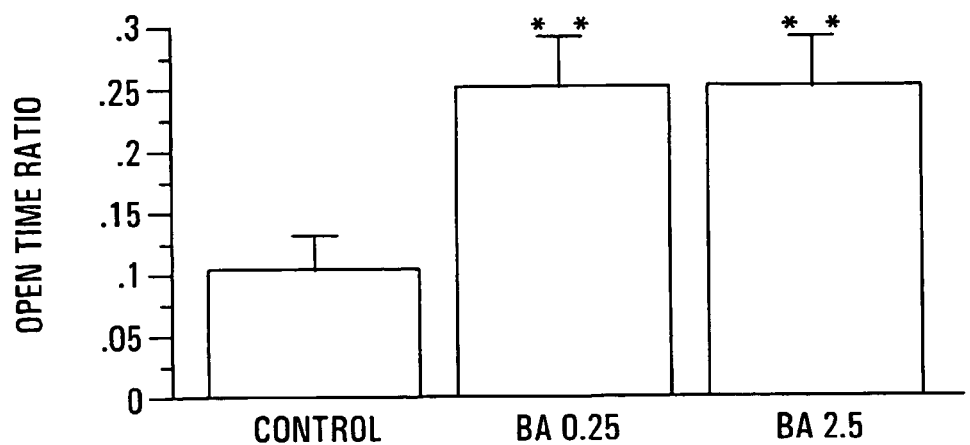
FIGS. 5a and 5b are bar graphs depicting the effect of betulinic acid (at 0.25 mg/kg and 2.5 mg/kg) on performance on the elevated plus maze (**Significantly different from control at $p<0.01$).
Figure 5B:
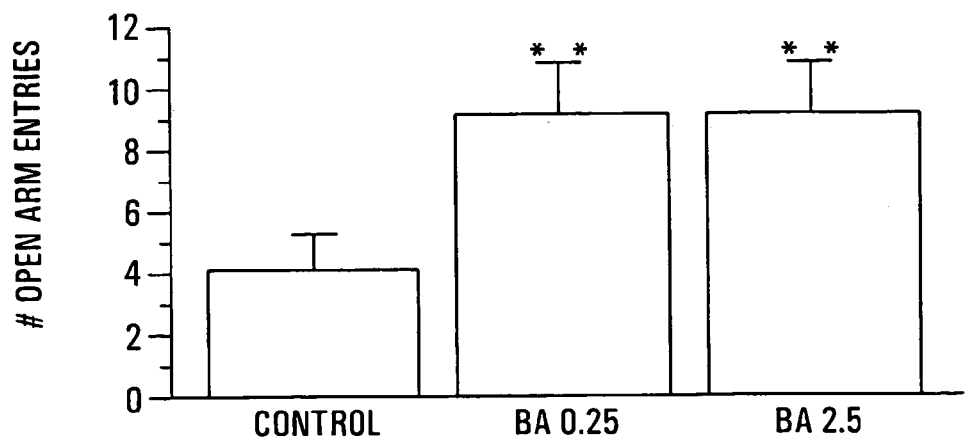

As can be seen in FIGS. 5*a* and 5*b*, mice treated with betulinic acid at either the 0.25 or 2.5 mg/kg i.p. dosage entered the open (anxiogenic) arm of the elevated plus maze more often than controls. The proportion of time spent on the open arm of the maze was also increased significantly.

It appears that for mice the 0.25 mg/kg dose may be the maximally effective dose (as a higher dose did not increase the anxiolytic effects further).

These data demonstrate that the anxiolytic effect of betulinic acid is not restricted to rats, as it can be observed in mice as well.

EXAMPLE 10

This example illustrates that betulinic acid reduces anxiety-like behaviours in BALB/c mice.

BALB/c mice represent a strain of mice that is very stress-reactive. It has been suggested that this strain may represent an animal model of trait anxiety.

Mice received dosages of betulinic acid in accordance with the previous example.

Figure 6A:
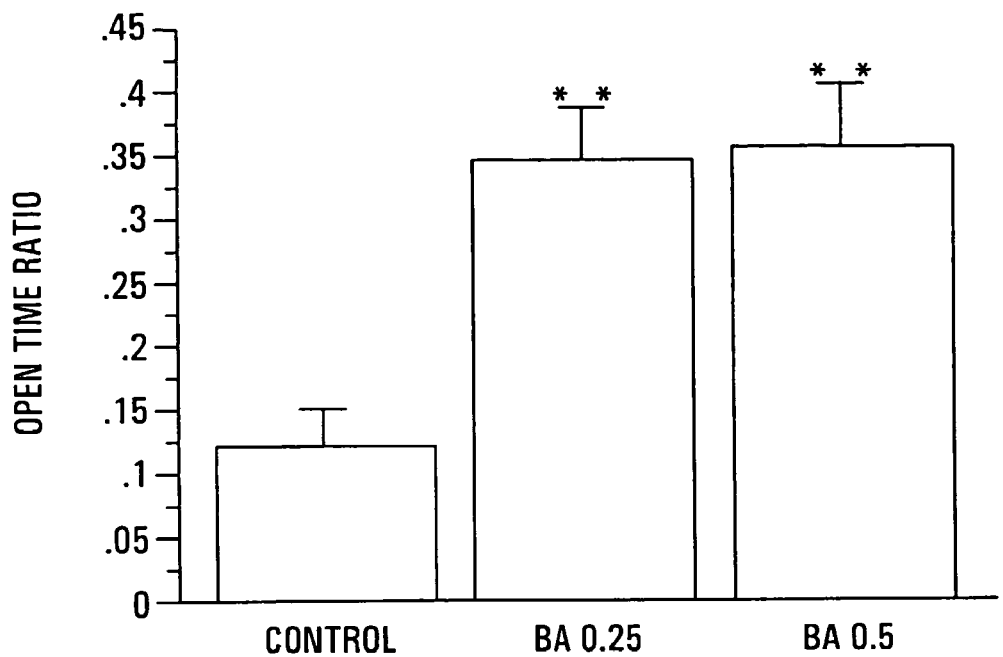
FIGS. 6a and 6b are bar graphs depicting the effect of betulinic acid (at 0.25 mg/kg and 2.5 mg/kg) on performance on the elevated plus maze in BALB/c mice (**Significantly different from control at $p<0.01$).
Figure 6B:
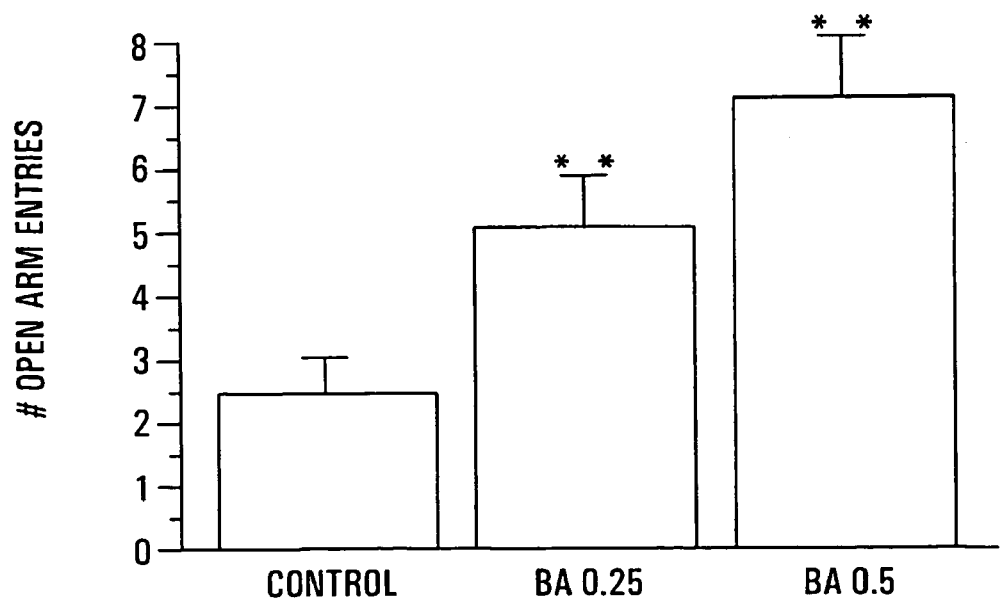

Betulinic acid had a pronounced effect on this strain of mice. As reflected in FIGS. 6*a* and 6*b*, both doses of betulinic acid (0.25 or 2.5 mg/kg; i.p.) significantly increased the proportion of time spent as well as the number of entries on the open arm of the elevated plus maze relative to the peanut oil only control.

Thus the anxiolytic effect of betulinic acid is evident in rats as well as mice. Furthermore, it seems effective in alleviating anxiety in a genetically anxious strain of mice.

These data also suggest that betulinic acid may potentially be effective in alleviating state as well as trait anxiety.

EXAMPLE 11

Figure 7:
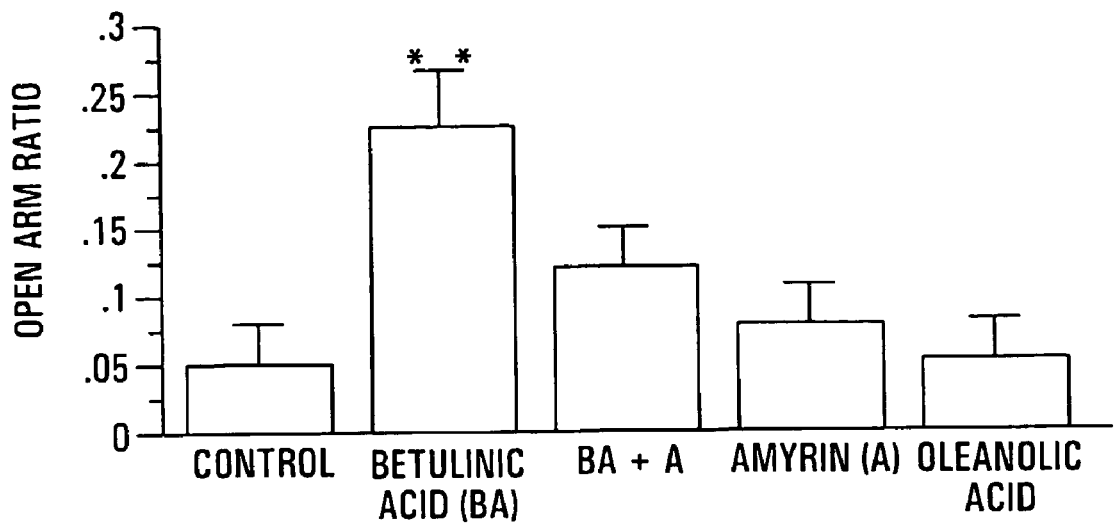
FIG. 7 is a bar graph depicting the effect of betulinic acid, beta-amyrin+betulinic acid, on performance on the elevated plus maze (**Significantly different from control at $p<0.01$).

This example compares the anxiolytic activity of betulinic acid and some other structurally related compounds. Results are illustrated in FIG. 7.

As expected, betulinic acid (0.5 mg/kg) increased the proportion of time spent in the open arm of the elevated plus maze.

However neither beta-amyrin (5 mg/kg) nor oleanolic acid (0.5 mg/kg), two compounds structurally related to betulinic acid, displayed any anxiolytic activity on the elevated plus maze paradigm. When betulinic acid and amyrin were administered together, no additive effect was seen.

EXAMPLE 12

This example compares the effect of betulinic acid and betulinic acid methyl ester on social interaction in rats.

The rat social interaction paradigm takes advantage of rats' natural behaviour in novel situations. The more 'anxious' the animals are, the less likely they are engage in social interaction with the cohort. Anxiolytic drugs typically increase the amount of time rodents spend socially interacting with one another. (File, S.E., (1980). The use of social interaction as a method for detecting anxiolytic activity of chlor-diazepoxide-like drugs. In *Current Protocols in Neuroscience* (pp. 8.3.3-8.3.4), John-Wiley & Sons).

The social-interaction (SI) test arena constituted of a 60×60 cm white Plexiglas floor, enclosed by 35-cm high walls of the same material. The arena was surrounded by black curtain, and a closed circuit camera was positioned above the setup, to feed live video signals to the experimenter seated in a separate room, for behavioral assessment and recording.

Each rat was placed alone in the SI box for 7.5 min daily for 2 days, in order to familiarize the animals with the test environment. Animals were paired according to their body weights (less than 10 g difference) and each pair was randomly assigned to one of the treatment groups. Rats received either betulinic acid 0.5 mg/kg i.p., betulinic acid methyl ester (methyl betulinate) 0.5 mg/kg i.p., or peanut oil only (control). Drugs were injected (i.p.) 60 min prior to testing. Tests were carried out at three intervals, 1 h, 2.5 h and 4 h after injection. Each pair was tested at the 1-h interval, then new pairs from within the same drug group were formed for the 2.5-h interval and then again at the 4-h interval (new pairs were formed for each test interval, to control for the potential confounding effect partner familiarity). At each of the three test intervals, animals were observed for 7.5 min. The behaviors scored included the amount of time the pairs spent interacting together (sniffing, grooming and chasing) as well as the number of times the animals initiated contact.

Figure 8:
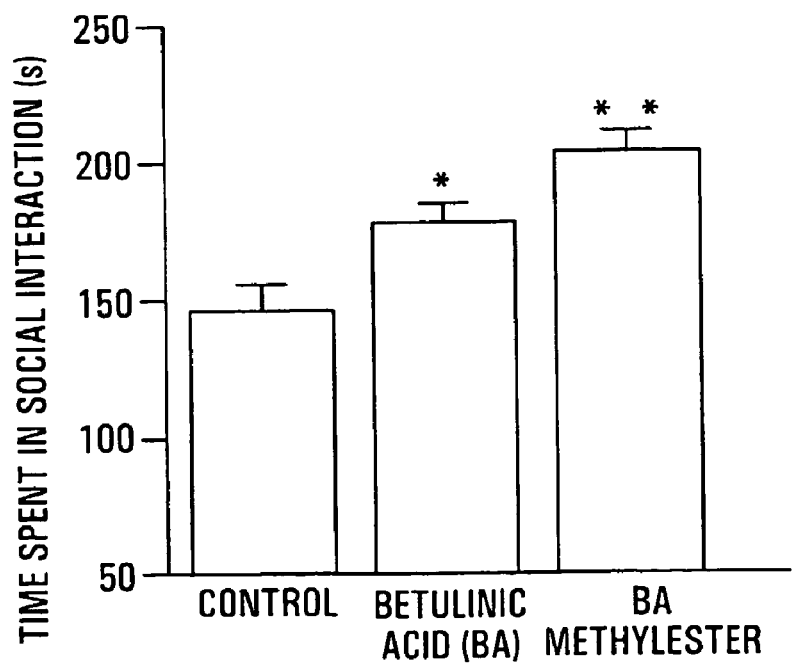
FIG. 8 is a bar graph comparing the effect of betulinic acid and its methyl ester on time spent (in seconds) relative to a control by pairs of rats in social interaction (*, **Significantly different from control at $p<0.05$ and $0.01$, respectively).

Data analysis of interaction time using ANOVA, indicated a significant main Treatment effect (F $(2,79)$=16.577, $p<0.0001$) but no Time effect (F $(2,79)$=0.882, $p>0.4$). Thus the data were collapsed across time and, as shown in FIG. 8, the analyses revealed that both betulinic acid ($p<0.001$) and its methyl ester derivative ($p<0.0001$) significantly increased the amount of social interaction when compared to the control group. Furthermore, betulinic acid methyl ester was also significantly more effective at increasing social interaction than betulinic acid ($p<0.05$). The frequency of initiated contact was found to be not significant.

EXAMPLE 13

This example compares the anxiolytic activity of betulonic acid and some synthesized derivatives of betulinic acid to the activity of diazepam, as tested in the Vogel (punished drinking) paradigm.

In the Vogel test, rats are water deprived overnight, prior to testing, and then given the opportunity to drink for 10 min in the test chamber. Every 5th lick is 'punished' with the delivery of a mild shock delivered through the drinking spout. This generates 'anxiety' due to the conflict between the desire to drink (due to the thirst) and the discomfort of the occasional shocks delivered through the waterspout. Thus the rats drink less when they are periodically shocked, than when they are not shocked. The number of licks made (or the shocks accepted) by the thirsty rat is known to be increased by drugs with anti-anxiety properties, and this test is one of the 'gold standards' accepted by drug companies. An anxiolytic effect is inferred if an animal persists in the drinking more than the matched controls, in the presence of waterspout shocks. (Vogel, J. R., Beer, B., & Cloudy, D. E., (1971). A simple and reliable conflict procedure for testing anti-anxiety agents., In *Current Protocols in Neuroscience* (pp 8.3.10-8.3.12), John-Wiley & Sons).

The Vogel setup (Coulbourn Instruments, Allentown, Pa.) comprised a clear Plexiglas cage (30×25×30 cm), which housed the animal during the test session. An external shock source was attached to the metal spout of the water bottle. An optical beam located at the base of the waterspout tracked the number of licks performed by monitoring the number of beam interruptions caused by the animal's tongue.

Animals maintained on a water deprivation schedule were allowed access to water only during a 1-h period once a day, and maintained on a restricted diet of 5 pellets a day of Purina Lab Chow. Drug dosages and route of administration were as in Example 12. Prior to the testing, the animals were familiarized with the test cages and waterspouts by allowing them to explore the cage and have shock-free access to the water for 10 min/day for 3 days. After each test session, the rats were given ad libitum access to water for 60 min. The rats were then placed into the apparatus for a 10 min test session. They were initially allowed shock-free access to water (for the first 5 s), after which the shock circuit was activated such that every 5th lick was accompanied by a shock (0.4 mA).

Figure 9A:
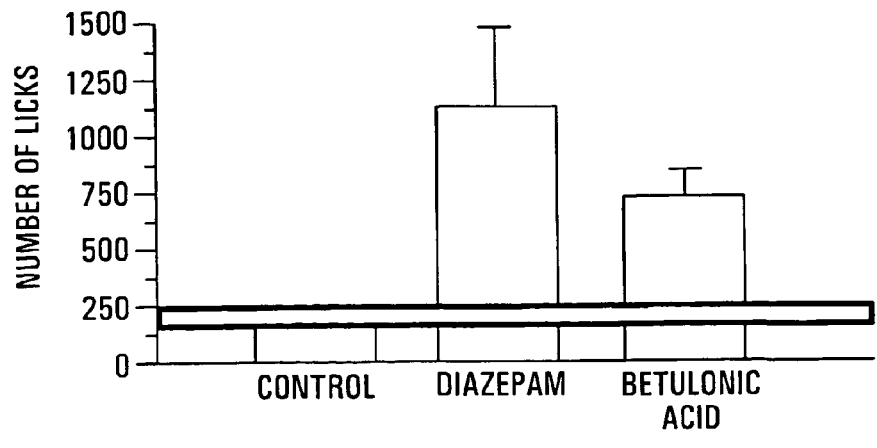
FIGS. 9a-9c are bar graphs illustrating the effects of various derivatives of betulinic acid on punished drinking (Vogel test) relative to diazepam.
Figure 9B:
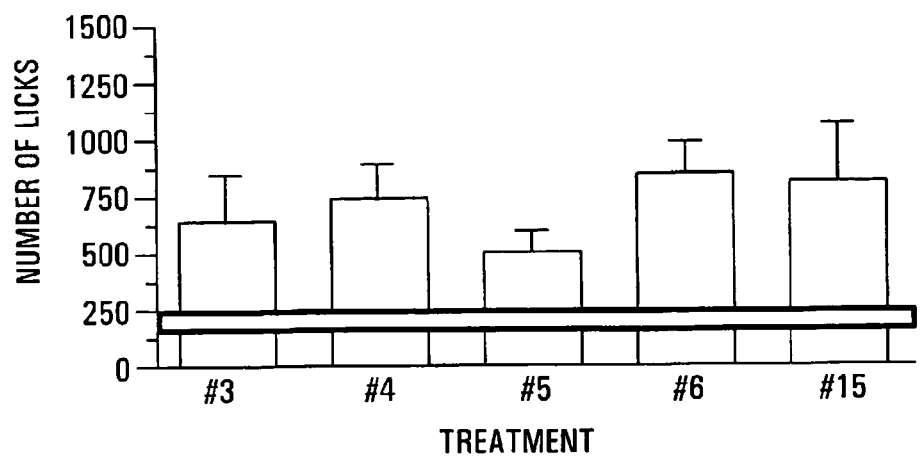
Figure 9C:
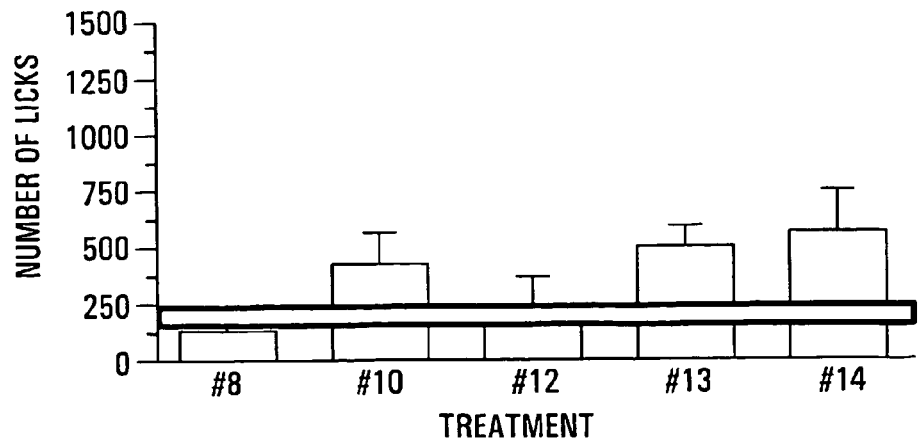

The results are illustrated in FIGS. 9a-9c. The treatment numbers correspond to the compounds listed in Table 1. Compounds which showed activity at a level above the horizontal bar are deemed to be reasonably active anxiolytics.

EXAMPLE 14

Many anxiolytics lose their efficacy as the subject quickly becomes tolerant to the drug. This example shows the effect of chronic administration of betulinic acid and betulinic acid methyl ester.

In an elevated-plus maze test as described in the preceding examples, adult male Sprague Dawley rats (350-375 g) were administered one of: (a) peanut oil vehicle (control); (b) betulinic acid dissolved in peanut oil (SS-01); or (c) methyl ester of betulinic acid dissolved in peanut oil (SS-01ME). The drugs were administered orally at a daily dose of 0.5 mg/kg. via gavage for ~30 days. Behavioural tests were conducted between days 21-30 of chronic exposure. Animals were administered the respective compounds one-hour prior to testing on the elevated plus maze. "Acute administration" constituted a single dose of the test compound in chronically-treated rats, one-hour before testing.

Figure 10:
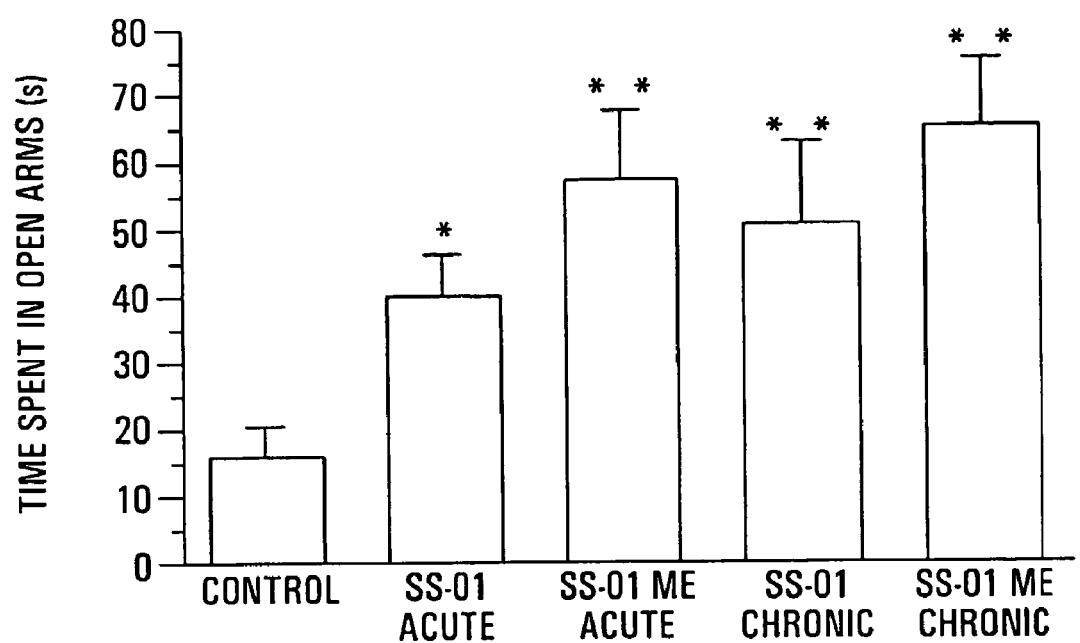
FIG. 10 is a bar graph illustrating the effect of acute and chronic treatments of betulinic acid and its methyl ester, relative to a control, on the time spent in the open arms of an elevated plus maze.

FIG. 10 shows the effects of chronic and acute drug administration on the time spent (seconds) in the open arms of the elevated plus maze. Acute administration of the drug to chronically treated rats maintained its anti-anxiety effects, as reflected by increased time spent on the open arms of the elevated plus maze. This indicates no tolerance or desensitisation development upon chronic treatment.

EXAMPLE 15

Many anxiolytics cause impairment of locomotor activity after chronic use. This example shows the effects of chronic administration of betulinic acid (SS01) and methyl ester of betulinic acid (SS01ME) on locomotor activity in rats.

Figure 11:
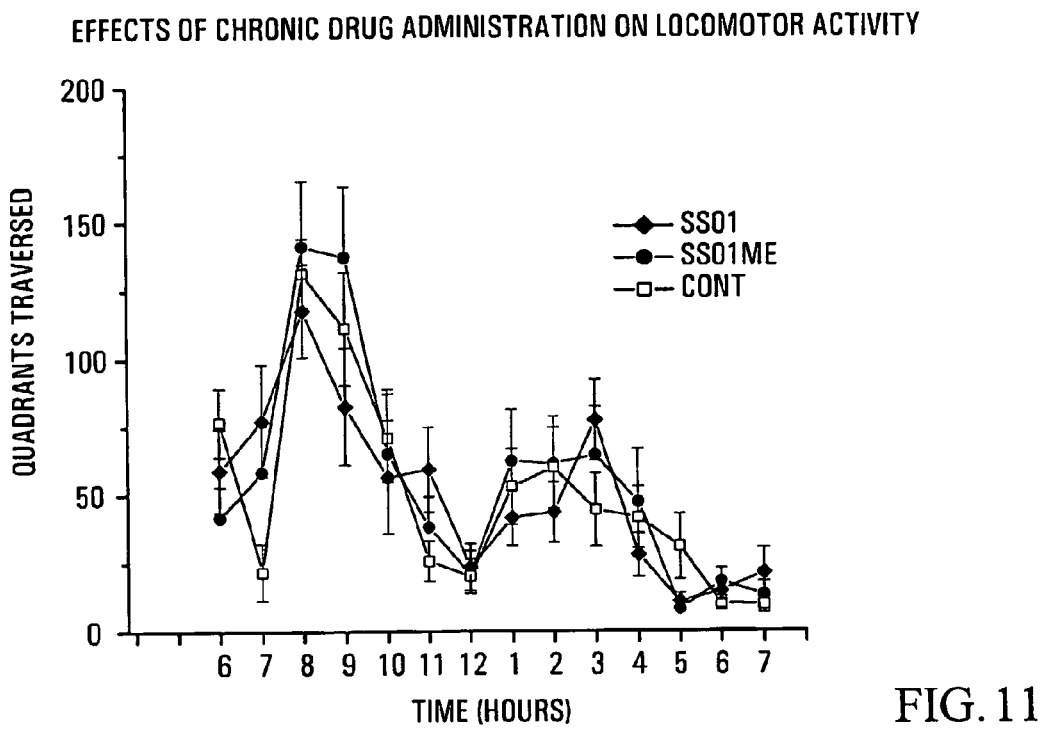
FIG. 11 is a graph illustrating the effect of chronic treatment with betulinic acid and its methyl ester, relative to a control, on locomotor activity.

Test animals and drug treatments were as in Example 14. Locomotor activity was recorded for one night (5 p.m. to 7 a.m. the following morning) in the control as well as in the betulinic acid and methyl ester of betulinic acid exposed groups. Locomotor activity was monitored using infrared sensors located on the roof of the animals' cage. Eight independent sensors monitored activity of animals according to the number of quadrants traversed. FIG. 11 shows the effects of chronic drug administration on locomotor activity for rats treated with the control, with betulinic acid (SS01), or with methyl ester of betulinic acid (SS01ME). The results show that neither betulinic acid nor the methyl ester of betulinic acid had an adverse effect on locomotor activity or pattern. Non-alteration of the locomotor activity or patterns suggest no adverse locomotor effect and/or sleep disturbances.

EXAMPLE 16

Figure 12:
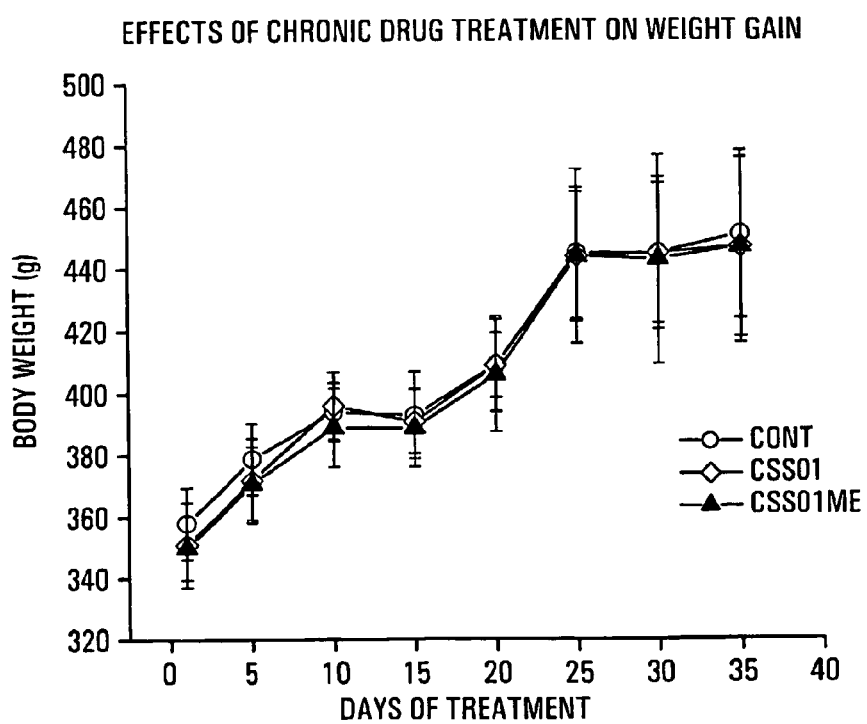
FIG. 12 is a graph illustrating the effect of chronic treatment with betulinic acid and its methyl ester, relative to a control, on weight gain.

The weight gain over the period of treatment was observed for rats treated with the control as well as rats treated with betulinic acid or its methyl ester (test animals and treatments as in Example 14). FIG. 12 shows the effects of chronic drug treatment on weight gain for rats treated with the control, with betulinic acid (CSS01) and with the methyl ester of betulinic acid (CSS01ME). Chronic drug treatment did not seem to affect weight gain in a significant manner.

EXAMPLE 17

This examples studied the results of cessation of chronic treatment of rats treated with betulinic acid or its methyl ester as in Example 14.

Upon cessation of chronic treatment, no overt withdrawal effects were observed over the following 48 hours. Behaviour monitoring was made every hour using time-sampling methods, for 48 consecutive hours.

EXAMPLE 18

Betulinic acid showed no signs of acute or chronic toxicity, even at repeated doses of up to 500 mg/kg. This is a dose 1000 times higher than that needed to reduce anxiety. The observed lack of toxicity is further corroborated by work that shows betulinic acid to be non-toxic in a Hippocratic screen at doses of 200 and 400 mg/kg.

EXAMPLE 19

Tests were conducted by MDS Panlabs to determine whether any of the classical neurotransmitter systems or the peptidergic systems thought to play a role in anxiety are affected by betulinic acid. The results showed that none of the following neurotransmitters or proteins were affected by betulinic acid:

| | |
|---|---|
| Catecholamines: | adrenergic $\alpha 1$, $\alpha 2$, and $\beta$; MAO A and B; |
| COMT: | NE transporter; domaine D1 and D2, DA transporter; |
| Gabaergic: | GABA transporter; $GABA_A$, agonist site; $GABA_A$, BZP; GABA Cl- channel; $GABA_B$; Glutamate non-selective; |
| Histamine: | Histamine H1, H2, and H3 |
| Serotonin (5-HT): | $5-HT_1$; $5-HT_{1A}$; $5-HT_2$; $5-HT_3$; serotonin transporter |
| Acetylcholine: | muscarinic non-selective; nicototinic; |
| Sigma: | Sigma non-selective |
| Peptides: | bombesin; cannabinoid $CB_1$ and $CB_2$; cholecystokinin (CCK); $CCK_A$; EGF; galanin $Gal_{R1}$ and $GAL_{R2}$; GLP-1; melanocortin MC4; neuropeptide $Y_1$ and $Y_2$; neurotensin; opiate non-selective; somatostatin; tachykinin $NK_1$, $NK_2$, and $NK_3$; TNF non-selective; VIP1; cyclooxygenase; COX-1 and COX-2; interleukin IL-1$\alpha$ |

EXAMPLE 20

This example illustrates the preparation of methyl betulinate (compound # 5).

An ether solution containing diazomethane was added to betulinic acid (100 mg, 0.22 mmole) dissolved in dichloromethane (50 mL) containing a few drops of methanol at 0° C. until the yellow colour of diazomethane persisted. The reaction mixture was stirred at room temperature overnight in the fume-hood to allow the excess diazomethane to evaporate. The solvent was removed in vacuo. The residue was re-dissolved in ethyl acetate (30 ml), washed successively with water (10 mL), brine (10.0 mL) and water (10 mL), dried over anhydrous magnesium sulfate, filtered then concentrated in vacuo. The crude product (100 mg) was recrystallized from hexane and chloroform to give 80 mg, 78% of a white solid, mp: 220-221° C., HRMS: Calculated for $C_{31}H_{50}O_3$, 470.3762; found: 470.37663.

EXAMPLE 21

This example illustrates the preparation of 3-acetoxybetulinic acid (compound #4).

A mixture of betulinic acid (1.12 g, 2.45 mmole), triethylamine (500 mg, 0.7 mL) and a catalytic amount of DMAP in 50 mL of dichloromethane was stirred for 10 minutes. Acetic anhydride (500 mg, 0.5 mL) was added and stirring was continued overnight at room temperature. The reaction mixture was washed successively with water (20 mL), 5% HCl (20 mL), water (20 mL), dried over anhydrous magnesium sulfate, filtered and concentrated under reduced pressure. The crude product was purified by silica gel chromatography to afford a white solid (810 mg, 66%), mp: 275-277° C. (from methanol), HRMS: Calculated for $C_{32}H_{50}O_4$: 498.3711; found: 498.37201.

EXAMPLE 22

This example illustrates the preparation of betulinic acid isobutyl amide (compound # 12).

The procedure for the preparation of this compound was adapted from the method of Evers, et al. *J. Med. Chem.*, (1996), 39:1056-1068. Other amides may be prepared similarly.

To a solution of 3-acetoxybetulinic acid (100 mg, 0.20 mmole) in dichloromethane (10.0 mL) was added first oxalyl chloride (38.2 mg, 0.03 mL), and then a few drops of DMF. The mixture was stirred at room temperature for 6 hours, concentrated in vacuo and re-dissolved in 2 mL of dichloromethane. The solution thus prepared was added drop-wise to a solution of isobutylamine (16.2 mg, 0.02 mL) and triethylamine (22.4 mg, 0.03 mL) in 8 mL of dichloromethane at 0° C. Stirring was continued for 1 hour. The reaction mixture was washed successively with water (5 mL), 1% HCl (5 mL) and water (5 mL), dried over anhydrous magnesium sulfate, filtered and concentrated in vacuo. The crude material was stirred overnight in 20 mL of methanol with excess potassium carbonate at 25-30° C. Methanol was removed in vacuo and the reaction mixture was re-dissolved in ethyl acetate (25 mL), washed with water (2×10 mL), dried over anhydrous magnesium sulfate then concentrated in vacuo. The crude product was purified by silica gel chromatography to afford a white solid (100 mg, 97%), mp: 216-217° C. (from methanol), HRMS: Calculated for $C_{34}H_{57}NO_2$: 511.43918; found: 511.44049.

EXAMPLE 23

This example illustrates the preparation of methyl dihydrobetulinate (compound #3).

A mixture of methyl betulinate (100 mg, 0.21 mmole) and 20 mg of 30% Pd on carbon in 25 mL of methanol was stirred under hydrogen overnight at room temperature. The reaction mixture was filtered and the residue was washed with methanol (2×10 mL) and then concentrated under reduced pressure. The crude product (100 mg) was recrystallized from methanol to give a white solid (80 mg, 80%), mp: 236-238° C., HRMS: Calculated for $C_{31}H_{52}O_3$: 472.39186; found: 472.39230.

EXAMPLE 24

This example illustrates the preparation of dihydrobetulinic acid (compound #15).

Betulinic acid (100 mg, 0.20 mmole) and 20 mg of Pd/C in 25 mL of methanol were stirred under hydrogen gas overnight at room temperature. The reaction mixture was filtered, washed with methanol (2×10 mL) and concentrated in vacuo. The crude product was recrystallized from methanol to give 79 mg of a white solid, mp: 297-299° C., HRMS: Calculated for $C_{30}H_{50}O_3$: 458.3762; found: 458.37656.

EXAMPLE 25

This example illustrates the preparation of betulinic acid esters (R=CH$_2$Ph, R=CH$_2$CO$_2$C$_2$H$_5$, R=C$_6$H$_{13}$, R=CH$_2$CH=CH$_2$, R=C$_2$H$_5$).

Sodium hydride (10 mol equivalent) was added to a solution of betulinic acid (100 mg) in THF (5 mL) at room temperature. The mixture was stirred for 30 minutes prior to the addition of appropriate alkyl halide (5 mol equivalent) and a catalytic amount of tetrabutylammonium iodide (10 mol %). The solution was stirred overnight at room temperature. The reaction mixture was quenched with water (20 mL) and THF was removed by rotary evaporation. The resulting mixture was extracted with ethyl acetate (3×20 mL). The combined organic extracts was washed with water (20 mL), dried (MgSO4), filtered and concentrated under reduced pressure. The residue was purified by silica gel chromatography using hexane-ethylacetate as eluant to give the desired ester in 33-91% yields. The assignment of the proton NMR peaks are base on analogy with spectral data reported by Siddiqui et. al., for betulinic acid and methyl betulinate. [J. Nat. Prod. 1988, Vol. 51, No. 2, 229]

Benzyl betulinate: [R=CH$_2$Ph in Formula II]

Yield: 75%, white solid, mp 187-189° C.

$^1$H NMR (200 MHz, CDCl3): δ: 7.32 (m, 5H, Ph), 5.14 (d, J=3.8 Hz, 2H, —CH2-Ph), 4.70 (s, 1H, H-29a), 4.57 (s, 1H, H-29b), 3.15 (dd, J=10.3 Hz, J=5.2 Hz, 1H, H-3á), 3.00 (ddd, J=11.0 Hz, J=4.9 Hz, 1H, H-19), 1.68 (s, 3H, H-30), 0.93 (s, 3H, H-27), 0.92 (s, 3H, H-26), 0.77 (s, 3H, H-23), 0.73 (s, 3H, H-25), 0.72 (s, 3H, H-24), [only readily assignable peaks are reported]; $^{13}$C NMR (200 MHz, CDCl3): δ: 175.7, 150.5, 136.4, 128.4, 128.2, 128.0, 109.5, 78.9, 65.7, 56.5, 55.3, 50.5, 49.4, 46.9, 42.3, 40.6, 38.8, 38.6, 38.1, 37.1, 36.9, 34.2, 32.0, 30.5, 29.5, 27.9, 27.3, 25.5, 20.8, 19.3, 18.2, 16.1, 15.8, 15.3, 14.6; MS (EI): 546 [M]+; HRMS: Calculated for $C_{37}H_{54}O_3$: 546.40720, found: 546.40621.

Ethyl acetoxy betulinate {R=CH$_2$—CO$_2$C$_2$H$_5$ in Formula II]

Yield: 76%, white fluffy solid, m. p. 66-68° C.

$^1$H NMR (200 MHz, CDCl3): δ: 4.70 (d, J=2.0 Hz, 1H, H-29a), 4.55 (s, 3H, H-29b and CO2-CH2-CO2), 4.19 (q, J=7.2 Hz, 2H, CH2-CO2) 3.15 (dd, J=10.4 Hz, J=5.4 Hz, 1H, H-3á), 2.95 (ddd, J=10.8 Hz, J=4.5 Hz, 1H, H-19), 1.66 (s, 3H, H-30), 0.94 (s, 3H, H-27), 0.93 (s, 3H, H-26), 0.90 (s, 3H, H-23), 0.79 (s, 3H, H-25), 0.72 (s, 3H, H-24) [only readily assignable peaks are reported]; $^{13}$C NMR (200 MHz, CDCl3): δ: 175.4, 168.0, 150.5, 109.6, 78.9, 61.3, 60.2, 56.5, 55.3, 50.5, 49.3, 46.7, 42.4, 40.7, 38.8, 38.7, 38.0, 37.1, 36.9, 34.2, 31.9, 30.4, 29.5, 27.9, 27.3, 25.5, 20.8, 19.3, 18.2, 16.1, 15.9, 15.3, 14.6, 14.1; MS (EI): 542 [M]+; HRMS: Calculated for $C_{34}H_{54}O_5$: 542.39712, found: 542.39682.

Hexyl betulinate [R=C$_6$H$_{13}$ in formula II]

Yield: 91%, white fluffy solid, m.p. 54-56° C.

$^1$H NMR (200 MHz, CDCl3): δ: 4.70 (d, J=1.6 Hz, 1H, H-29a), 4.57 (s, 1H, H-29b), 4.04 (m, 2H, CH2-CO2) 3.16 (dd, J=9.9 Hz, J=5.5 Hz, 1H, H-3á), 3.00 (ddd, J=10.8 Hz, J=4.8 Hz, 1H, H-19), 1.66 (s, 3H, H-30), 0.94 (s, 3H, H-27), 0.89 (s, 3H, H-26), 0.86 (s, 3H, H-23), 0.79 (s, 3H, H-25), 0.73 (s, 3H, H-24) [only readily assignable peaks are reported]; $^{13}$C NMR (200 MHz, CDCl3): δ: 176.3, 150.7, 109.5, 78.9, 64.0, 56.5, 55.3, 50.5, 49.4, 47.0, 42.4, 40.7, 38.8, 38.7, 38.3, 37.1, 37.0, 34.3, 32.2, 31.8, 30.6, 29.6, 28.9, 28.7, 28.0, 27.4, 26.1, 25.5, 22.6, 20.9, 19.3, 18.3, 16.1, 16.0, 15.3, 14.7; MS (EI): 554 [M]+; HRMS: Calculated for $C_{37}H_{62}O_3$: 554.46990, found: 554.47083

Allyl betulinate. [R=CH$_2$CH=CH$_2$ in Formula II]

Yield: 89%, white fluffy solid, m. p. 65-68° C.

$^1$H NMR (200 MHz, CDCl3): δ: 5.90 (m, 1H, CH=), 5.26, (ddd, J=17.2 Hz, J=10.3 Hz, J=1.4 Hz, 2H, CH2=) 4.70 (s, 1H, H-29a), 4.54 (br s, 3H, H-29b and CH2-CO2), 3.15 (dd, J=10.2 Hz, J=5.5 Hz, 1H, H-3á), 3.00 (ddd, J=11.1 Hz, J=3.9 Hz, 1H, H-19), 1.65 (s, 3H, H-30), 0.93 (s, 6H, H-27 and H-26), 0.88 (s, 3H, H-23), 0.79 (s, 3H, H-25), 0.72 (s, 3H, H-24).) [only readily assignable peaks are reported]; $^{13}$C NMR (200 MHz, CDCl3) δ: 175.7, 150.6, 132.5, 118.1, 109.6, 78.9, 64.6, 56.5, 55.3, 50.5, 49.4, 46.9, 42.3, 40.7, 38.8, 38.7, 38.1, 37.1, 37.0, 34.3, 32.1, 30.5, 29.6, 27.9, 27.4, 25.5, 20.8, 19.3, 18.2, 16.1, 15.9, 15.3, 14.7; MS (EI): 496.4 [M; HRMS: Calculated for $C_{33}H_{52}O_3$: 496.39165, found: 496.39220.

Ethyl betulinate [R=C$_2$H$_5$ in Formula II]

Yield: 33%, white solid, m. p. 193-195° C.

$^1$H NMR (200 MHz, CDCl3): δ: 4.70 (s, 1H, H-29a), 4.57 (s, 1H, H-29b), 4.11 (m, 2H, —CH2-CO2), 3.16 (dd, J=10.3 Hz, J=5.4 Hz, 1H, H-3á), 3.00 (ddd, J=10.7 Hz, J=4.6 Hz, 1H, H-19), 1.65 (s, 3H, H-30), 0.94 (s, 6H, H-27 and H-26), 0.89

(s, 3H, H-23), 0.79 (s, 3H, H-25), 0.73 (s, 3H, H-24) [only readily assignable peaks are reported]; $^{13}$C NMR (200 MHz, CDCl3) δ: 171.1, 150.7, 109.5, 78.9, 59.8, 56.4, 55.3, 50.5, 49.4, 47.0, 42.4, 40.7, 38.8, 38.7, 38.2, 37.1, 37.0, 34.3, 32.1, 30.6, 29.6, 28.0, 27.4, 25.5, 20.9, 19.4, 18.3, 16.1, 15.9, 15.3, 14.7, 14.3; MS (EI): 484. [M]+; HRMS. Calculated for $C_{32}H_{52}O_3$: 484.39165, found: 484.38990

Example 26

This example illustrates the preparation of betulinic acid amides. Oxalyl chloride (1.5 mol equiv.) and 1 drop of DMF were added to a solution of 3-acetoxybetulinic acid (100 mg) in $CH_2Cl_2$ (10 mL). The solution was stirred for 6 h at room temperature. The solvent and the DMF were removed in vacuo. The remaining material was re-dissolved in $CH_2Cl_2$ (1-2 mL) and added dropwise to a solution containing the appropriate amine (1.1 mol equivalent) and triethyl amine (1.1 mol equivalent) in $CH_2Cl_2$ (8 mL) at 0° C. Stirring was continued for 1 h. The reaction mixture was then washed with water (5.0 mL), 1% HCl (5 mL), water (5 mL), dried ($MgSO_4$), filtered and concentrated under reduced pressure. Deprotection of the hydroxyl group was achieved by stirring the resulting 3-acetoxy amide of betulinic acid in methanol (20 mL) containing excess $K_2CO_3$ at 30-35° C. overnight. The reaction mixture was filtered and concentrated under reduced pressure. The crude product was subjected to silica gel chromatography using hexane-ethyl acetate as eluant to afford the desired amide.

Betulinic acid N-benzyl amide
Yield: 64%, white solid, m.p. 239-242° C.
$^1$H NMR (500 MHz, CDCl$_3$) δ: 7.29 (m, 5H, Ph), 5.85 (t, 1H, J=5.7 Hz, N—H), 4.72 (d, 1H, J=2.0 Hz, H-29a), 4.58 (d, 1H, J=2.1 Hz, H-29b), 4.47 (dd, 1H, J=14.7 Hz, J=5.8 Hz, CH-Ph), 4.35 (dd, 1H, J=14.0 Hz, J=5.6 Hz, CH-Ph), 3.16 (m, 2H, H-3a and H-19), 1.67 (s, 3H, H-30), 0.94 (s, 6H, H-27 and H-26), 0.89 (s, 3H, H-23), 0.80 (s, 3H, H-25), 0.74 (s, 3H, H-24) [Only readily assignable hydrogens are reported]; $^{13}$C NMR (500 MHz, CDCl$_3$) δ: 175.9, 150.9, 139.2, 128.7, 127.8, 127.3, 109.3, 76.7, 55.7, 55.4, 50.7, 50.2, 46.7, 43.3, 42.5, 40.8, 38.9, 38.8, 38.4, 37.8, 37.2, 34.5, 33.8, 30.9, 29.9, 29.5, 27.9, 27.4, 25.7, 20.9, 19.5, 18.3, 16.2, 15.3, 14.7; IR (CHCl$_3$, cm$^{-1}$): 3447.6, 2942.4, 2867.9, 2360.2, 2342.3, 1638.0, 1522.3, 1454.5, 1375.6, 1189.4, 982.4, 884.1, 756.7, 698.5, 668.4; MS (EI): 545 [M]+; HRMS. Calculated for $C_{37}H_{55}NO_2$: 545.42329. Found: 545.42218

Betulinic acid N-isobutyl amide
Yield: 97%, white solid, m. p. 216-217° C.
$^1$H NMR (500 MHz, CDCl$_3$) δ: 5.61 (t, 1H, J=5.8 Hz, N—H), 4.71 (d, 1H, J=2.2 Hz, H-29a), 4.56 (d, 1H, J=2.3 Hz, H-29b), 3.12 (m, 13H, CH2-N), 2.98 (m, 1H, H-19), 1.65 (s, 3H, H-30), 0.91 (s, 3H, H-27), 0.89 (s, 1H, H-26), 0.88 (s, 3H, H-23), 0.79 (s, 3H, H-25), 0.73 (s, 3H, H-24) [Only readily assignable hydrogens are reported]; $^{13}$C NMR (500 MHz, CDCl$_3$) δ:175.9, 150.9, 109.2, 78.9, 55.6, 55.4, 50.6, 50.1, 46.7, 46.6, 42.5, 40.7, 38.8, 38.7, 38.5, 37.7, 37.2, 34.4, 33.9, 30.9, 29.4, 28.7, 27.9, 27.4, 25.6, 20.9, 20.2, 20.1, 19.4, 18.3, 16.1, 16.0, 15.3, 14.6; IR (CHCl$_3$, cm$^{-1}$): 3449, 2949., 2869, 2361., 2343, 1638., 1509, 1388., 1195, 1044, 983, 909, 882., 733; MS (EI): 511. [M]+; HRMS. Calculated for $C_{34}H_{57}NO_2$: 511.43918. Found: 511.44049.

Betulinic acid N-pyrrolidine
Yield: 78%, white solid, m.p. 223-226° C.
$^1$H NMR (200 MHz, CDCl$_3$) δ: 4.69 (d, 1H, J=2.2 Hz, H-29a), 4.54 (s, 1H, H-29b), 3.40 (m, 4H, 4×CH2—N), 3.09 (m, 2H, Ha and H-19), 1.65 (s, 3H, H-30), 0.93 (s, 6H, H-27 and H-26), 0.91 (s, 3H, H-23), 0.79 (s, 3H, H-25), 0.72 (s, 3H, H-24) [Only readily assignable hydrogens are reported]; $^{13}$C NMR (500 MHz, CDCl$_3$) δ:173.6, 151.6, 108.9, 78.9, 55.4, 52.4, 50.8, 46.3, 42.0, 40.6, 38.8, 38.7, 38.6, 37.2, 37.1, 35.2, 34.4, 31.2, 30.8, 29.7, 27.9, 27.4, 25.6, 21.1, 19.6, 18.3, 16.2, 15.3, 14.7; IR (CHCl$_3$, cm$^{-1}$): 3424, 3070, 2942, 2868, 2362, 1607, 1451, 1406, 1390, 1375, 1246, 1214, 1187, 1168, 1137, 1108, 1045, 982, 917, 881, 754, 665; MS (EI): 5109. [M]+; HRMS. Calculated for $C_{34}H_{55}NO_2$: 509.42329. Found: 509.42312

EXAMPLE 27

This example illustrates the preparation of the sodium salt of betulinic acid.

Betulinic acid (370 mg) was then dissolved in methanol (200 mL) with warming before and 2 mL of 0.41 M sodium methoxide solution (2 mL) was added. The solvent was removed via a rotary evaporation and a white solid was obtained (370 mg), m.p.291-295° C. Its solubility was greater in water and in methanol than pure betulinic acid.

EXAMPLE 28

This example illustrates the epoxidation of the methyl betulinate.

To a stirred solution of methyl ester of betulinic acid (100 mg, 0.213 mmol) in $CH_2Cl_2$ (10 mL) was added sodium acetate (100 mg, 1.22 mmol). The solution was cooled to 0° C. and peracetic acid (0.2 mL, 2.97 mmol) was added. The ice bath was then removed and the reaction mixture was stirred for 3 h before the reaction was quenched with 15% solution of $Na_2SO_3$ (20 mL). The solvent was removed in vacuo and then extracted with ethyl acetate (3×20 mL). The combined organic extracts were washed successively with a saturated solution of $K_2CO_3$ (2×20 mL) and brine (20 mL) before it was dried ($MgSO_4$) filtered and concentrated under reduced pressure. The crude product was purified by silica gel chromatography using hexane-ethyl acetate as eluant to give the desired product as a white solid (80 mg, 77%).

$^1$H NMR (200 MHz, CDCl$_3$) δ: 3.60 (s, 3H, O—CH3), 3.15 (dd, J=10.4 Hz, J=5.5 Hz, 1H, H-3a), 2.60 (d, J=2.1 Hz, 2H, H-29), 1.20 (s, 3H, H-30), 0.92 (s, 3H, H-27), 0.91 (s, 3H, H-26), 0.86 (s, 3H, H-23), 0.79 (s, 3H, H-25), 0.72 (s, 3H, H-24) [only the readily assignable peaks are reported]; $^{13}$C NMR (200 MHz, CDCl$_3$) δ: 176.4, 78.8, 60.1, 56.8, 56.5, 55.2, 51.3, 50.3, 50.1, 45.4, 42.3, 40.6, 38.8, 38.7, 37.4, 37.1, 36.8, 34.2, 32.0, 29.3, 27.9, 27.3, 27.0, 26.8, 20.9, 18.3, 18.2, 16.0, 15.8, 15.3, 14.5; MS (EI): 486.4 [M]+

EXAMPLE 29

This example illustrates the epoxidation of 3-β-acetoxy betulinic acid.

To a solution of 3-acetoxy betulinic acid (530 mg, 1.06 mmol) in $CH_2Cl_2$ (20 mL) at 0° C. was added mCPBA (280 mg, 1.60 mmol). The ice-bath was removed and the solution was stirred at room temperature overnight. The reaction mixture was then washed successively with 10% solution of NaHSO3 (2×10 mL), saturated solution of Na2CO3 (2×10 mL) and brine (2×10 mL) then dried (MgSO4), filtered and concentrated under reduced pressure. The crude product was purified by silica gel chromatography using hexane-ethyl acetate as the eluant yielding the target epoxide as a white solid (280 mg, 51%), m.p. 290-293° C.

$^1$H NMR (200 MHz, CDCl$_3$) δ: 4.44 (dd, 1H, J=9.3 Hz, J=6.4 Hz, 1H, H-3a), 2.64 (s, 2H, H-29), 2.02 (s, 3H, CH$_3$—CO$_2$), 1.22 (s, 3H, H-30), 0.93 (s, 3H, H-27), 0.89 (s, 3H, H-26), 0.83 (s, 3H, H-23), 0.82 (s, 3H, H-25), 0.81 (s, 3H, H-24) [only the readily assignable peaks are reported]; $^{13}$C NMR (200 MHz, CDCl$_3$) δ: 182.2, 171.1, 80.9, 60.2, 56.6, 55.3, 50.2, 49.9, 45.4, 42.3, 40.7, 40.6, 38.3, 37.7, 37.5, 37.0, 36.8, 34.1, 31.9, 29.3, 27.9, 26.9, 26.7, 23.6, 21.3, 20.8, 18.1, 18.0, 16.4, 16.1, 16.0, 14.5.

EXAMPLE 30

This example illustrates the hydroboration of methyl betulinate.

To a solution of methyl betulinate (200 mg, 0.43 mmol) in dry THF (15 mL) at room temperature was added borane-methyl sulfide (0.08 mL, 0.85 mmol). After 7 h, 3N NaOH (0.43 mL) was added followed by 30% W/W $H_2O_2$ while keeping the temperature between 30-35° C. and then slowly warmed to 50° C. The reaction mixture was then stirred overnight at 50-60° C., then diluted with diethyl ether (20 mL), washed with brine (10 mL), dried ($MgSO_4$), filtered and concentrated in vacuo. The crude material was purified by silica gel chromatography using hexane-ethyl acetate as eluant to yield the desired product (140 mg, 67%), m.p. 220° C.-223° C.

$^1$H NMR (200 MHz, $CDCl_3$) δ: 3.76 (dd, 1H, J=10.3 Hz, J=4.6 Hz, 1H, H-29), 3.62 (s, 3H, O—$CH_3$), 3.39 (dd, J=10.5 Hz, J=8.0 Hz, 1H, H-29), 3.17 (dd, J=10.1 Hz, J=5.6 Hz, 1H, H-3a), 1.32 (s, 3H, H-30), 0.94 (s, 3H, H-27), 0.92 (s, 3H, H-26), 0.88 (s, 3H, H-23), 0.80 (s, 3H, H-25), 0.73 (s, 3H, H-24) [only the readily assignable peaks are reported];
$^{13}$C NMR (200 MHz, $CDCl_3$) δ: 176.6, 78.9, 64.2, 56.8, 55.2, 51.2, 50.2, 48.7, 43.1, 42.5, 40.6, 38.8, 38.6, 38.3, 38.1, 37.1, 37.0, 34.3, 32.0, 29.6, 27.9, 27.3, 27.2, 23.8, 20.9, 18.2, 18.1, 16.0, 15.9, 15.4, 14.6; IR ($CHCl_3$, $cm^{-1}$): 3386, 2948, 2870, 1716, 1455, 1390, 1377, 1319, 1290, 1272, 1217, 1189.2, 1167.1, 1136.6, 1105.9, 1040.7, 982.5, 945.8, 757.1, 666.6.

MS (EI): 488.4 [M]+

HRMS: Calculated for $C_{31}H_{52}O_4$, 488.38656, found 488.38549.

EXAMPLE 31

This example illustrates the ozonolysis of betulinic acid and preparation of platanic acid.

Ozone was passed through a solution of betulinic acid (200 mg, 0.44 mmol) in 5% solution of $MeOH/CH_2Cl_2$ at 78° C. for 30 minutes. The reaction was then quenched with dimethyl sulfide (2 mL) and the solvent was removed by rotary evaporation. The reaction mixture was re-dissolved in ethyl acetate (100 mL) and washed with water (2×10 mL), dried ($MgSO_4$), filtered and concentrated to dryness in vacuo. The crude product was purified by silica gel chromatography using hexane-ethyl acetate as eluant to afford the desired compound (120 mg, 60%), m.p. 278-282° C., lit. 279-282° C. (J. Nat. Prod. 1994, Vol. 57, 249).

$^1$H NMR (500 MHz, $CDCl_3$) δ: 3.20 (m, 2H, H-3a, H-19), 2.15 (s, 3H, H-30), 0.98 (s, 3H, H-27), 0.94 (s, 3H, H-26), 0.89 (s, 3H, H-23), 0.80 (s, 3H, H-25), 0.73 (s, 3H, H-24) [only the readily assignable peaks are reported]; $^{13}$C NMR (200 MHz, $CDCl_3$) δ: 212.2, 181.3, 78.9, 56.2, 55.3, 51.2, 50.3, 49.2, 42.2, 40.6, 38.8, 38.6, 37.5, 37.2, 36.7, 34.2, 31.4, 30.1, 29.7, 28.3, 28.0, 27.3, 27.2, 20.8, 18.2, 16.1, 15.9, 15.3, 14.7; IR ($CHCl_3$, $cm^{-1}$): 3467, 2944, 2871, 1702, 1561, 1452, 1388, 1378, 1357, 1279, 1239, 1189, 1170.4, 1137.6, 1108.2, 1074, 734, 647; MS (EI): 458 [M]+; HRMS. Calculated for $C_{29}H_{46}O_4$: 458.33963. Found: 458.33860.

EXAMPLE 32

This example illustrates the preparation of methyl platanate. Diazomethane was added to a solution of platanic acid in $CH_2Cl_2$ (50 mL) containing a few drops of methanol until the reaction mixture remained permanently yellow. Excess diazomethane was allowed to evaporate in the fumehood at room temperature overnight before the solvent was removed in vacuo. The crude product obtained after evaporation of the solvents was purified by silica gel chromatography using hexane-ethyl acetate as eluant to yield the desired compound (50 mg, 60%), m.p. 250-251° C., lit. 250-251° C. (J. Chem Soc., 1963, 3269).

$^1$H NMR (200 MHz, $CDCl_3$) δ: 3.65 (s, 3H, O—$CH_3$), 3.20 (m, 2H, H-3a, H-19), 2.15 (s, 3H, H-30), 0.98 (s, 3H, H-27), 0.94 (s, 3H, H-26), 0.89 (s, 3H, H-23), 0.80 (s, 3H, H-25), 0.73 (s, 3H, H-24) [only the readily assignable peaks are reported]; $^{13}$C NMR (200 MHz, $CDCl_3$) δ: 212.4, 176.5, 78.8, 56.4, 55.2, 51.4, 51.1, 50.3, 49.4, 42.1, 40.5, 38.8, 38.6, 37.3, 37.1, 36.6, 34.1, 31.4, 30.1, 29.7, 28.2, 27.9, 27.3, 27.2, 20.8, 18.2, 16.0, 15.8, 15.3, 14.7; MS (EI): 472. [M]+; HRMS: Calculated for $C_{30}H_{48}O_4$: 472.35528. Found: 472.35078.

EXAMPLE 33

This example illustrates the preparation of methyl 3-acetoxy platanate. Diazomethane was added to a solution of 3-acetoxy platanic acid (100 mg, 0.2 mmol) in $CH_2Cl_2$ (50 mL) containing a few drops of methanol until the reaction mixture remained permanently yellow. Excess CH2N2 was allowed to evaporate in the fumehood at room temperature overnight before the solvent was removed in vacuo. The crude product was purified by silica gel chromatography using hexane-ethyl acetate as eluant to yield the desired compound (80 mg, 78%), m.p. 204-206° C., lit. 205-207° C. (Coll. Czech. Chem. Comm., 1970, Vol. 35, 298).

$^1$H NMR (200 MHz, $CDCl_3$) δ: 4.44 (dd, 1H, J=9.8 Hz, J=6.2 Hz, H-3a), 3.64 (s, 3H, O—$CH_3$), 3.22 (t, 1H, J=10.7 Hz, H-19), 2.15 (s, 3H, H-30), 2.01 (s, CH3-CO2), 0.96 (s, 3H, H-27), 0.86 (s, 3H, H-26), 0.81 (s, 3H, H-23), 0.80 (s, 6H, H-25, H-24) [only the readily assignable peaks are reported]; $^{13}$C NMR (200 MHz, $CDCl_3$) δ: 212.3, 176.5, 171.0, 80.8, 56.3, 55.3, 51.4, 51.1, 50.2, 49.3, 42.1, 40.5, 38.2, 37.7, 37.2, 37.0, 36.5, 34.0, 31.4, 30.1, 29.6, 28.2, 27.8, 27.1, 25.6, 21.3, 20.8, 18.1, 16.4, 16.1, 15.8, 14.6; IR ($CHCl_3$, $cm^{-1}$): 2947, 2871, 1728, 1453, 1432, 1391, 1368, 1353, 1330, 1318, 1222, 1189, 1167, 1154, 1136, 1108, 1027, 980, 900, 757, 668; MS (EI): 514 [M]+; HRMS. Calculated: for $C_{32}H_{50}O_5$, 514.36586, found: 514.36725.

EXAMPLE 34

This example illustrates preparation of 3-Acetoxy platanic acid N-benzylamide.

Oxalyl chloride (0.03 mL, 0.30 mmol) and a few drops of DMF were added to a solution of 3-Acetoxy platanic acid (100 mg, 0.20 mmol) in $CH_2Cl_2$ (5 mL) at room temperature.

The solution was stirred for 6 h and the solvent and DMF were then removed by evaporation under reduced pressure. The reaction mixture was re-dissolved in $CH_2Cl_2$ (5 mL) and then added dropwise to a solution containing benzylamine (0.02 mL, 0.22 mmol) and triethylamine (0.03 mL, 0.22 mmol) in $CH_2Cl_2$ (5 mL) at 0° C. and stirring continued for 1 h. The reaction mixture was then washed with water (5 mL), 1% HCl (5 mL), water (5 mL), dried (MgSO4), filtered and concentrated in vacuo. Purification of the product was achieved by silica gel column chromatography using hexane-ethyl acetate as eluant to yield a white solid (60 mg, 51%).

$^1$H NMR (500 MHz, $CDCl_3$) δ: 7.30 (m. 5H, Ph), 5.91 (t, 1H, 5.7 Hz, N—H), 4.44 (dt, 2H, J=913.6 Hz, J=5.7 Hz, CH-Ph and H-3a), 4.32 (dd, 1H, J=14.7 Hz, J=5.6 Hz, CH-Ph), 3.46 (dt, 1H, J=11.3, J=4.4 Hz, H-19), 2.15 (s, 3H, H-30), 2.01 (s, CH3-CO2), 0.96 (s, 3H, H-27), 0.86 (s, 3H, H-26), 0.82 (s, 3H, H-23), 0.81 (s, 3H, H-25), 0.80 (s, 3H, H-24) [only the readily assignable peaks are reported]; $^{13}$C NMR (500 MHz, $CDCl_3$) δ: 212.9, 175.7, 170.9, 139.0, 128.7, 127.8, 127.4, 80.9, 55.5, 55.4, 51.0, 50.4, 50.0, 43.3, 42.3, 40.7, 38.4, 38.0, 37.8, 37.1, 36.8, 34.3, 33.0, 29.5, 28.6, 27.9, 27.2, 23.7, 21.3, 20.9, 18.2, 16.5, 16.2, 16.1, 14.7; IR ($CHCl_3$, cm−1): 3376, 2946, 2869, 1733, 1713., 1647, 1522, 1467, 1454, 1422, 1391, 1369, 1317, 1248, 1195, 1162, 1139, 1108, 1080, 916, 732, 699, 668, 647; MS (EI): 589 [M]+; HRMS: Calculated for $C_{38}H_{55}NO_4$,: 589.41332. Found: 589.4140.

EXAMPLE 35

This example illustrates the preparation of methyl dihdroplatanate.

To a solution of methyl platanate (50 mg, 0.11 mmole) in methanol/THF (3:1 mL) at 0° C. was added NaBH$_4$ (40 mg, 1.1 mmol) and the reaction was stirred at room temperature overnight. The reaction was quenched with NH$_4$Cl solution (5 mL) and the solvent removed in vacuo. The residue was extracted with ethyl-acetate (2×10 mL) and the combined organic extracts was then washed with water (5 mL), brine (5 mL), water (5 mL) before it was dried (MgSO$_4$), filtered and concentrated under reduced pressure. The crude product was purified by silica gel chromatography using hexane-ethyl acetate as eluant yielding a white solid as the major product and isomer (30 mg, 60%), m.p. 194-196° C.

$^1$H NMR (200 MHz, CDCl$_3$) δ: 3.84 (q, 1H, J=6.3 Hz, H-20), 3.63 (s, 3H, O—CH3), 3.17 (dd, 1H, J=10.4 Hz, J=5.6 Hz, H-3a), 0.94 (s, 6H, H-27, and H-26), 0.88 (s, 3H, H-23), 0.80 (s, 3H, H-25), 0.73 (s, 3H, H-24) [only the readily assignable peaks are reported];

$^{13}$C NMR (200 MHz, CDCl$_3$) δ: 176.9, 78.9, 68.9, 56.9, 55.2, 51.2, 50.2, 47.9, 45.6, 42.4, 40.6, 38.8, 38.6, 37.9, 37.1, 37.0, 34.3, 31.7, 29.6, 27.9, 27.3, 27.0, 23.3, 22.2, 20.8, 18.3, 16.1, 15.9, 15.4, 14.7; IR (CHCl$_3$, cm$^{-1}$): 3407, 2945, 2869, 1714, 1655, 1561, 1454, 1390, 1376, 1320, 1275, 1217, 1189, 1166, 1135, 1106, 1090, 1045, 1034, 1002, 983, 944, 919, 811, 757; MS (EI): 474 [M]+; HRMS. Calculated for $C_{30}H_{50}O_4$: 474.37090: Found 474.37130.

EXAMPLE 36

This example illustrates the preparation of methyl 3-acetoxydihydroplatanate.

To a solution of 3-acetoxy methylplatanate (110 mg, 0.21 mmole) in methanol/THF (9:3 mL) at 0° C. was added NaBH$_4$ (81 mg, 2.10 mmol) and the reaction was stirred at room temperature overnight. The reaction was quenched with NH$_4$Cl solution (10 mL) and the solvent removed in vacuo. The residue was extracted with ethyl-acetate (2×20 mL) and the combined organic extracts was then washed with water (10 mL), brine (10 mL), water (10 mL) before it was dried (MgSO$_4$), filtered and concentrated under reduced pressure. The crude product was purified by silica gel chromatography using hexane-ethyl acetate as eluant yielding a white solid as the major product and isomer (60 mg, 54%), m.p. 255-259° C.

$^1$H NMR (500 MHz, CDCl$_3$) δ: 4.45 (dd, 1H, J=10.8, J=5.5 Hz, H-3a), 3.88 (q, J=6.4 Hz, 1H, H-20), 3.63 (s, 3H, O—CH$_3$), 2.02 (s, CH$_3$—CO$_2$), 0.94 (s, 3H, H-27), 0.88 (s, 3H, H-26), 0.83 (s, 3H, H-23), 0.82 (s, 3H, H-25), 0.81 (s, 3H, H-24) [only the readily assignable peaks are reported]; $^{13}$C NMR (200 MHz, CDCl$_3$) δ: 176.9, 171.1, 81.0, 68.9, 56.9, 55.3, 51.2, 50.1, 47.9, 45.6, 42.4, 40.6, 38.3, 38.0, 37.7, 37.0, 34.3, 31.7, 29.6, 27.9, 27.0, 23.6, 23.3, 22.2, 21.3, 20.8, 18.3, 16.4, 16.1, 15.9, 14.6; IR (CHCl$_3$, cm$^{-1}$): 3538, 2947, 2871, 1720, 1655, 1561, 1458, 1392, 1370, 1318, 1248, 1189, 1135, 1107, 1030, 980, 945, 901, 857, 756, 665; MS (EI): 516 [M]+; HRMS: Calculated for $C_{30}H_{50}O_4$: 516.38166, Found: 516.38129.

Unless defined otherwise all technical and scientific terms used herein have the same meaning as commonly understood to one of ordinary skill in the art to which this invention belongs.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for treating anxiety in a subject, said method comprising administering to a subject in need thereof, a therapeutically effective amount of a betulinic acid-containing preparation obtained from a plant of the family Marcgraviaceae.

2. The method according to claim 1, wherein said preparation is an extract of Marcgraviaceae, prepared by a method comprising the steps of:
   (a) contacting a Marcgraviaceae plant or part thereof, with a solvent in which betulinic acid is soluble, to form a betulinic acid-containing extract; and,
   (b) recovering said extract.

3. The method according to claim 1, said preparation comprising at least 0.5% by weight betulinic acid.

4. The method according to claim 1, said preparation comprising at least 1% by weight betulinic acid.

5. The method according to claim 1, said preparation comprising at least 5% by weight betulinic acid.

6. The method according to claim 1, wherein said plant is of the genus *Souroubea* or *Schwartzia*.

7. The method according to claim 1, wherein said plant is a *Souroubea* species selected from the group consisting of *Souroubea gilgii*, *Souroubea sympetala*, *Souroubea loczyi*, *Souroubea venosa*, and *Souroubea vallicola*.

8. The method according to claim 1, wherein said preparation comprises a pharmaceutical composition, nutritional supplement, food product or beverage.

9. The method according to claim 1, wherein said preparation is administered in an amount sufficient to provide from 0.1 to 2.5 mg betulinic acid/kg of body weight of said subject per dose.

10. The method according to claim 1, wherein said preparation is administered in an amount sufficient to provide from 0.1 to 0.25 mg betulinic acid/kg of body weight of said subject per dose.

11. The method according to claim 1, wherein said anxiety is acute anxiety.

12. The method according to claim 1, wherein said anxiety is chronic anxiety.

13. The method according to claim 1, wherein said preparation is administered daily for a period of at least 21 days.

* * * * *

UNITED STATES PATENT AND TRADEMARK OFFICE
CERTIFICATE OF CORRECTION

PATENT NO.        : 7,488,722 B2
APPLICATION NO.   : 10/476716
DATED             : February 10, 2009
INVENTOR(S)       : Durst et al.

It is certified that error appears in the above-identified patent and that said Letters Patent is hereby corrected as shown below:

Title Page;
Please insert the following at page 1, column 1, between headers (87) and (65):

--Related U.S. Application Data
(60) Provisional application Nos. 60/290,035, filed on May 11, 2001; and 60/290,022, filed on May 11, 2001.--

Please replace the following citation on page 1, column 2, under "OTHER PUBLICATIONS":

"Chaudhuri, P.K., "Constituents of the Flowers of *Echinops Echinatus*" Fitoterapia, (1988), vol. 59, No. 2, p. 150-151, 5 REF. ISSN: 0367-326X, XP001096391, Cent. Inst. Medical & Aromatic Plants, Lucknow 226 016, India. abstract."

with the following citation:

"Chaudhuri, P.K., "Constituents of the Flowers of *Echinops Echinatus*" Fitoterapia, (1988), vol. 59, No. 2, p. 150-151, 5 REF. ISSN: 0367-326X, XP001096391, Cent. Inst. Medicinal & Aromatic Plants, Lucknow 226 016, India. abstract."

Please replace the following citation on page 2, column 2, under "OTHER PUBLICATIONS":

"Pisha et al., *Discovery of Betulinic Acid as a Selective Inhibitor of Human Melanoma that Functions by Induction of Apoptosis, 1(10): 1046-1051 (1995).*"

with the following citation:

"Pisha et al., *Discovery of Betulinic Acid as a Selective Inhibitor of Human Melanoma that Functions by Induction of Apoptosis, Nature Medicine 1(10):1046-1051 (1995).*"

Signed and Sealed this
Seventh Day of June, 2011

David J. Kappos
*Director of the United States Patent and Trademark Office*

CERTIFICATE OF CORRECTION (continued)

U.S. Pat. No. 7,488,722 B2

Please replace the chemical structure " 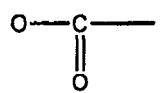 " at column 5, line 63-65 with the following structure: " 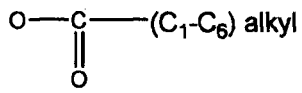 ".

Please delete "($C_1$-$C_6$ alkyl)" at column 6, line 1.